(12) United States Patent  
Petersen

(10) Patent No.: US 7,837,713 B2
(45) Date of Patent: Nov. 23, 2010

(54) METHODS AND SURGICAL KITS FOR MINIMALLY-INVASIVE FACET JOINT FUSION

(75) Inventor: David A. Petersen, Clearwater, FL (US)

(73) Assignee: minSURG International, Inc., Clearwater, FL (US)

( * ) Notice: Subject to any disclaimer, the term of this patent is extended or adjusted under 35 U.S.C. 154(b) by 139 days.

(21) Appl. No.: 12/404,273

(22) Filed: Mar. 13, 2009

(65) Prior Publication Data

US 2009/0234397 A1 Sep. 17, 2009

Related U.S. Application Data

(63) Continuation-in-part of application No. 12/238,255, filed on Sep. 25, 2008, which is a continuation-in-part of application No. 11/232,519, filed on Sep. 22, 2005, now Pat. No. 7,708,761, which is a continuation-in-part of application No. 10/992,720, filed on Nov. 22, 2004, now abandoned.

(51) Int. Cl.
*A61B 17/70* (2006.01)

(52) U.S. Cl. .................................................. 606/247

(58) Field of Classification Search .......... 606/247–249, 606/246, 59–60; 623/17.11–17.16
See application file for complete search history.

(56) References Cited

U.S. PATENT DOCUMENTS 736,738 A 8/1903 Frederick
3,848,601 A 11/1974 Ma et al.
4,501,269 A 2/1985 Bagby
4,834,757 A 5/1989 Brantigan
4,878,915 A 11/1989 Brantigan
4,961,740 A 10/1990 Ray
5,015,247 A 5/1991 Michelson
5,443,514 A 8/1995 Steffee
5,489,307 A 2/1996 Kuslich et al.
5,527,312 A 6/1996 Ray
D374,283 S 10/1996 Michelson (Continued)

OTHER PUBLICATIONS

*Frontier Devices, Inc. v. minSURG Corporation, Inc.*, Complaint, Jul. 2, 2010.

(Continued)

*Primary Examiner*—Alvin J Stewart
(74) *Attorney, Agent, or Firm*—Don J. Pelto; Sheppard, Mullin, Richter & Hampton LLP

(57) ABSTRACT

Disclosed herein are methods and surgical kits that can be used to fuse facet joints via a minimally invasive procedure (including an arthroscopic or percutaneous procedure). An exemplary method includes creating an incision; locating a facet joint with a distal end of a pin; sliding a substantially hollow drill guide over said pin wherein said drill guide comprises a proximal end, a distal end; removing said pin from within said drill guide; inserting a drill bit into said drill guide; drilling a hole into a bone of said facet joint; removing said drill bit; inserting a facet joint bone plug into said hole using a bone plug inserter having a raised portion at or near is proximal end, wherein said raised portion prevents over-insertion of said bone plug; and removing said drill guide.

21 Claims, 33 Drawing Sheets

U.S. PATENT DOCUMENTS

| | | | |
|---|---|---|---|
| 5,591,235 | A | 1/1997 | Kuslich |
| 5,645,598 | A | 7/1997 | Brosnahan |
| 5,683,391 | A | 11/1997 | Boyd |
| 5,700,291 | A | 12/1997 | Kuslich et al. |
| 5,772,661 | A | 6/1998 | Michelson |
| 5,782,919 | A | 7/1998 | Zdeblick et al. |
| 5,797,909 | A | 8/1998 | Michelson |
| 5,803,904 | A | 9/1998 | Mehdizadeh |
| 5,885,299 | A | 3/1999 | Winslow et al. |
| 5,888,224 | A | 3/1999 | Beckers et al. |
| 5,895,427 | A | 4/1999 | Kuslich et al. |
| 5,899,908 | A | 5/1999 | Kuslich et al. |
| 6,004,326 | A | 12/1999 | Castro |
| 6,063,088 | A | 5/2000 | Winslow |
| 6,080,158 | A | 6/2000 | Lin |
| 6,083,225 | A | 7/2000 | Winslow et al. |
| 6,086,595 | A | 7/2000 | Yonemura et al. |
| 6,113,602 | A | 9/2000 | Sand |
| 6,139,551 | A | 10/2000 | Michelson et al. |
| 6,146,420 | A | 11/2000 | McKay |
| 6,200,322 | B1 | 3/2001 | Branch et al. |
| 6,264,657 | B1 | 7/2001 | Urbahns |
| 6,283,966 | B1 | 9/2001 | Houfburg |
| 6,485,518 | B1 | 11/2002 | Cornwall et al. |
| 6,520,967 | B1 | 2/2003 | Cauthen |
| 6,524,312 | B2 | 2/2003 | Landry et al. |
| 6,610,065 | B1 | 8/2003 | Branch et al. |
| 6,991,654 | B2 | 1/2006 | Foley |
| 7,223,269 | B2 | 5/2007 | Chappuis |
| 7,320,688 | B2 | 1/2008 | Foley et al. |
| D566,277 | S | 4/2008 | Barry |
| D574,495 | S | 8/2008 | Petersen |
| 7,452,369 | B2 | 11/2008 | Barry |
| 7,517,358 | B2 | 4/2009 | Petersen |
| 7,699,878 | B2 * | 4/2010 | Pavlov et al. ............... 606/279 |
| 7,708,761 | B2 | 5/2010 | Petersen |
| 2001/0039388 | A1 | 11/2001 | Korotko et al. |
| 2002/0077641 | A1 | 6/2002 | Michelson |
| 2003/0004530 | A1 | 1/2003 | Reo |
| 2003/0149438 | A1 | 8/2003 | Nichols et al. |
| 2004/0097929 | A1 | 5/2004 | Branch et al. |
| 2005/0267482 | A1 | 12/2005 | Hyde |
| 2006/0036243 | A1 | 2/2006 | Sasso et al. |
| 2006/0041311 | A1 | 2/2006 | McLeer |
| 2006/0064099 | A1 | 3/2006 | Pavlov et al. |
| 2006/0085068 | A1 | 4/2006 | Barry |
| 2006/0111779 | A1 | 5/2006 | Petersen |
| 2006/0125814 | A1 | 6/2006 | Asai et al. |
| 2006/0276790 | A1 | 12/2006 | Dawson |
| 2007/0282220 | A1 | 12/2007 | Abernathie |
| 2008/0015701 | A1 | 1/2008 | Garcia et al. |
| 2008/0234758 | A1 * | 9/2008 | Fisher et al. ................ 606/309 |
| 2009/0030459 | A1 | 1/2009 | Hoy et al. |
| 2009/0036927 | A1 * | 2/2009 | Vestgaarden ................ 606/247 |
| 2009/0125066 | A1 | 5/2009 | Kraus et al. |
| 2009/0131986 | A1 * | 5/2009 | Lee et al. .................... 606/247 |
| 2009/0157119 | A1 | 6/2009 | Hale |
| 2009/0182377 | A1 | 7/2009 | Petersen |
| 2009/0216274 | A1 | 8/2009 | Morancy-Meister et al. |
| 2010/0114166 | A1 | 5/2010 | Kohm et al. |
| 2010/0137910 | A1 * | 6/2010 | Cawley et al. .............. 606/247 |

OTHER PUBLICATIONS

*Frontier Devices, Inc.* v. *minSURG Corporation, Inc.*, Amended Complaint, Jul. 27, 2010.
*Frontier Devices, Inc.* v. *minSURG Corporation, Inc.*, Memorandum in Support of Motion to Dismiss, Jul. 29, 2010.
*minSURG International, Inc.* v. *Nuvasive, Inc. et al.*, Complaint, Jul. 19, 2010.
*minSURG International, Inc.* v. *Nuvasive, Inc. et al.*, Exhibits to Complaint (patents), Jul. 19, 2010.
*minSURG International, Inc.* v. *Nuvasive, Inc. et al.*, Brief in Support of Motion for Preliminary Injunction, Aug. 3, 2010.
*VG Innovations, Inc.* v. *minSURG Corporation, Inc.*, Complaint, Jul. 6, 2010.
*VG Innovations, Inc.* v. *minSURG Corporation, Inc.*, Notice of Removal, Aug. 3, 2010.
*NuFix, Inc.* v. *minSURG Corporation, Inc.*, Complaint, Jun. 29, 2010.
*NuFix, Inc.* v. *minSURG Corporation, Inc.*, Exhibits (patents), Jun. 29, 2010.
*NuFix, Inc.* v. *minSURG Corporation, Inc.*, Memorandum in Support of Motion to Dismiss, Jul. 22, 2010.

* cited by examiner

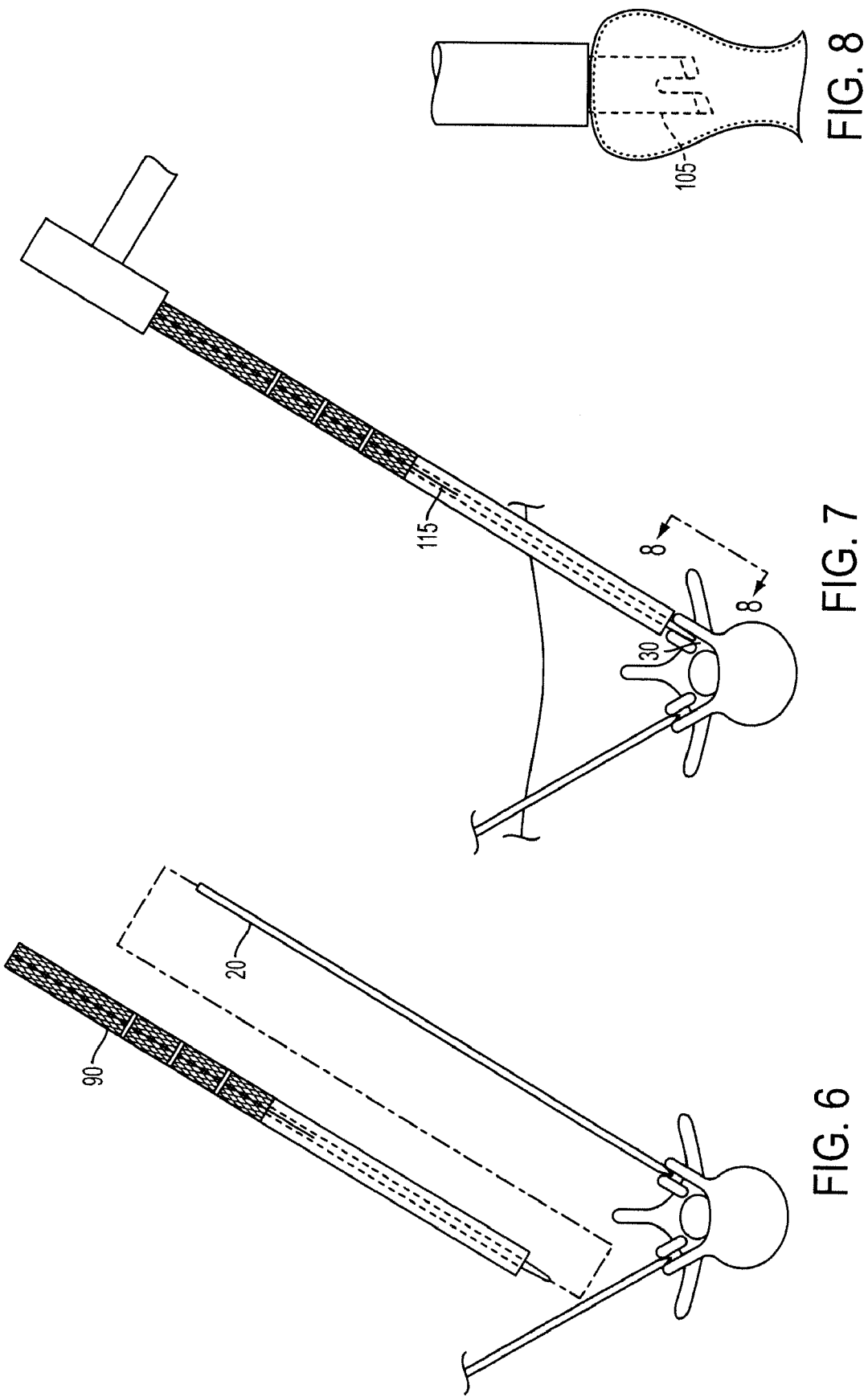

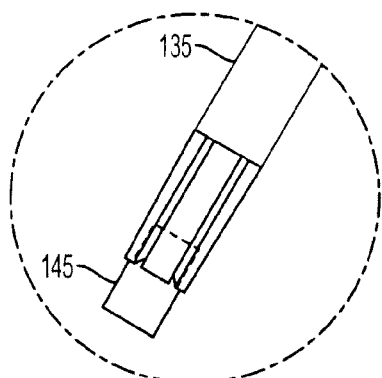
FIG. 13
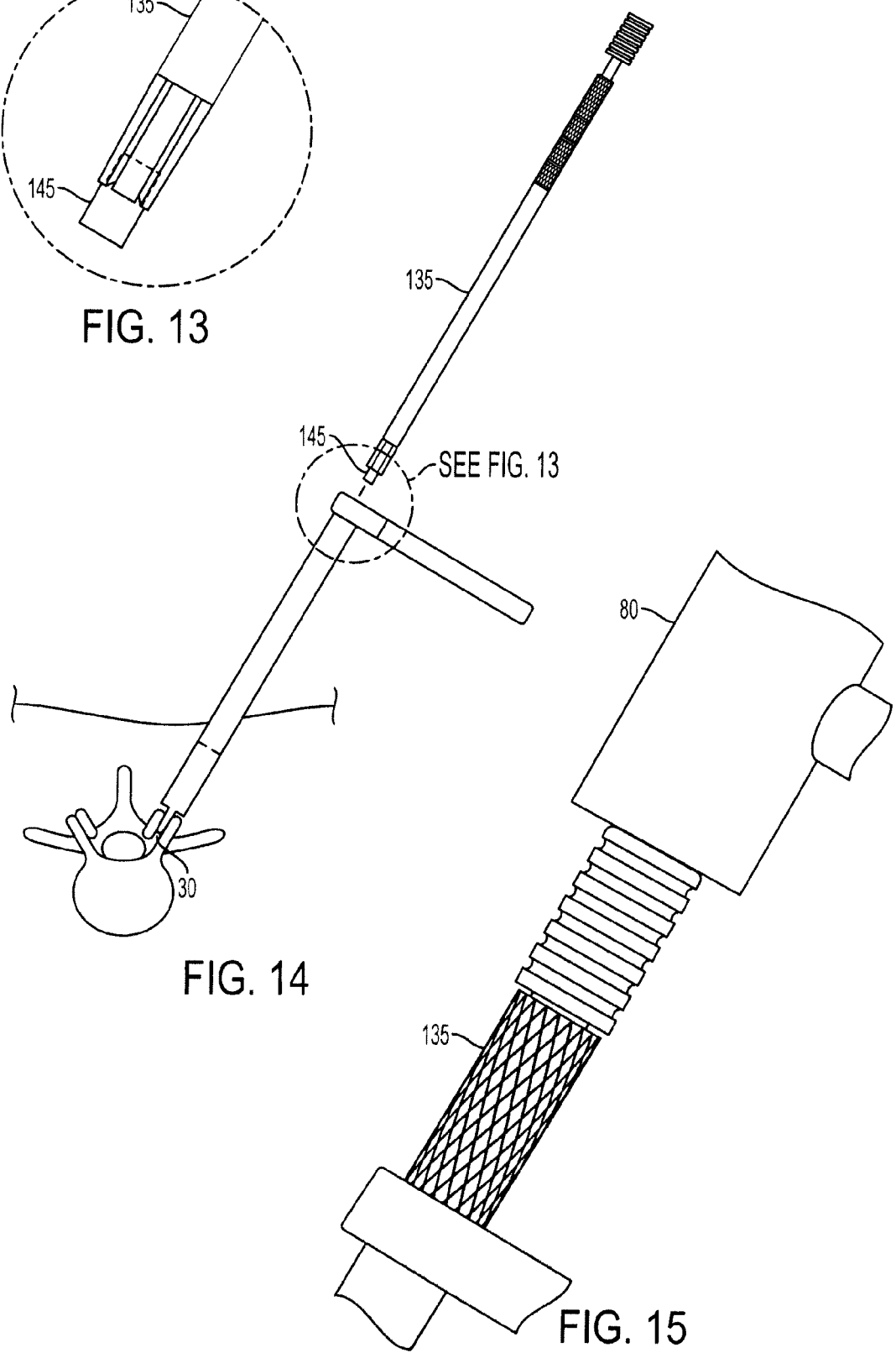
FIG. 14
FIG. 15

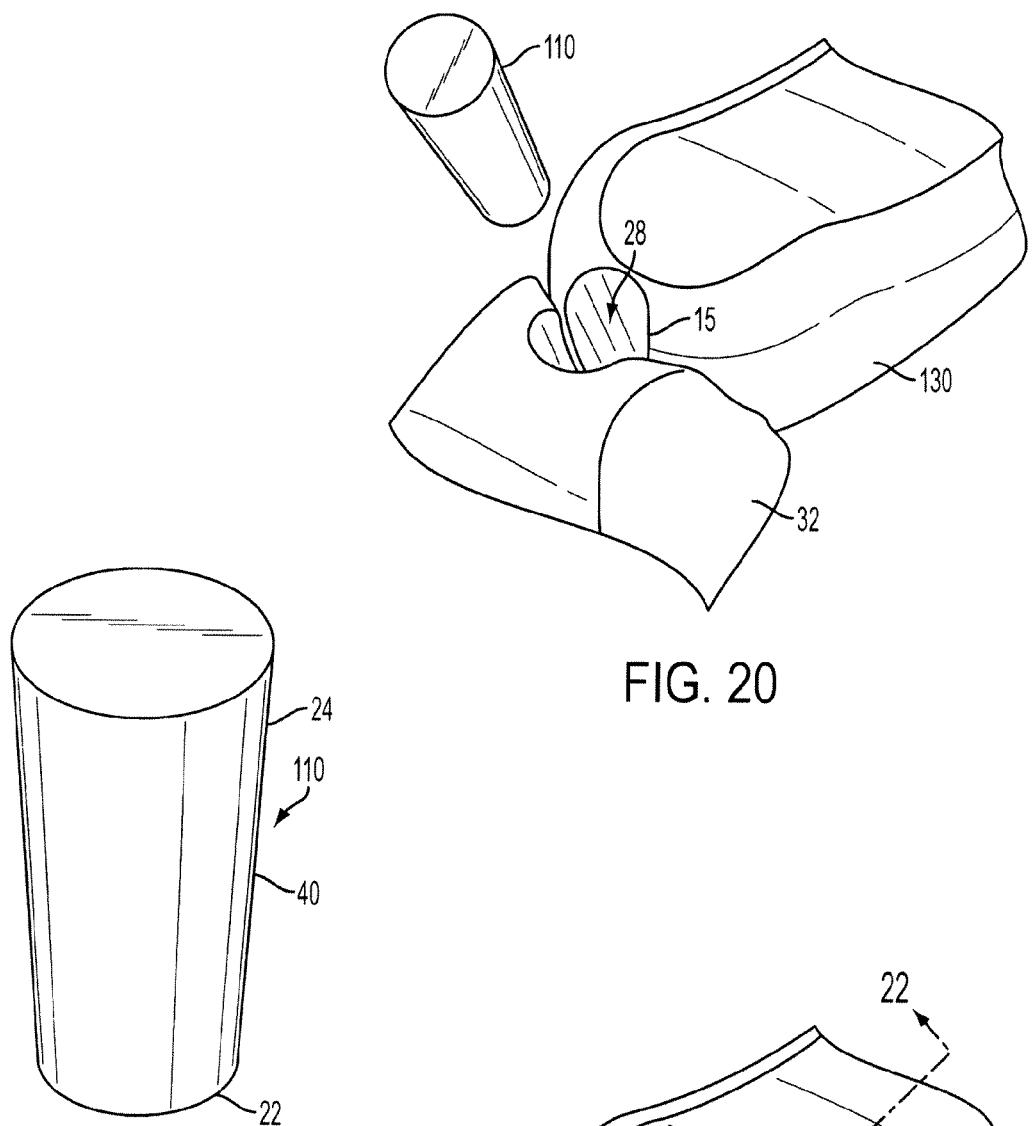
FIG. 20
FIG. 21
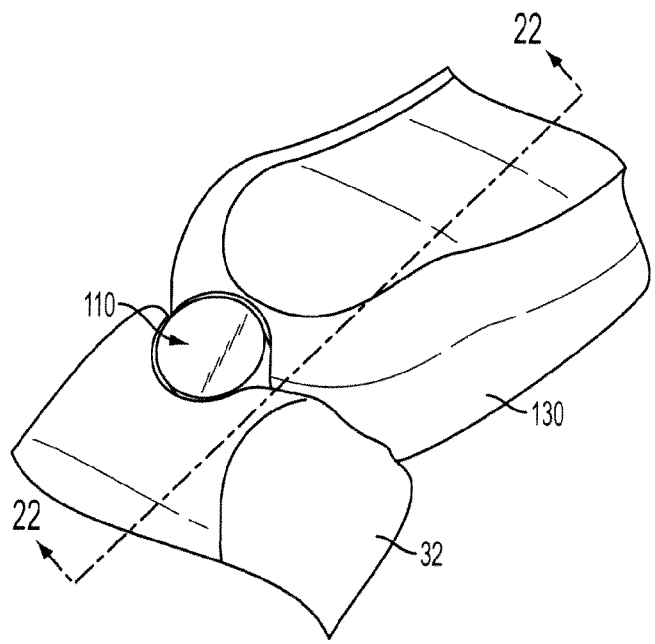
FIG. 22

METHODS AND SURGICAL KITS FOR MINIMALLY-INVASIVE FACET JOINT FUSION

PRIOR APPLICATIONS

This application is a continuation-in-part of U.S. patent application Ser. No. 12/238,255 filed Sep. 25, 2008, which is continuation-in-part of application Ser. No. 11/232,519 filed Sep. 22, 2005 now U.S. Pat. No. 7,708,761 which is a continuation-in-part of U.S. patent application Ser. No. 10/992,720, filed Nov. 22, 2004 now abandoned.

FIELD OF THE INVENTION

The present invention relates to methods and surgical kits that can be used to fuse facet joints through minimally invasive procedures.

BACKGROUND OF THE INVENTION

In the United States, about 10% of the population will suffer from back pain sometime in the next year. This occurrence is more than any other injury or disease except for the common cold and flu. About one-third of those suffering from back pain will not recover and will live with persistent, disabling symptoms. These numbers are cumulative year after year.

One root cause of back pain, particularly the persistent and disabling kind, is problems (including arthritis) with facet joints. The back of each vertebra has two sets of facet joints. One pair faces upward and the other pair faces downward. Within each set there is a facet joint on the left side of each vertebra and a facet joint on the right side of each vertebra.

Facet joints are the system of joints that allow movement (forward bending, backward bending and twisting) of the spine. While these joints allow movement of the spine, their interlocking nature also helps to stabilize the spine.

Similar to other joints in the body, each facet joint is surrounded by a capsule of connective tissue and produces synovial fluid to nourish and lubricate the joint. The joint surfaces themselves are coated with a thick spongy material called articular cartilage that enables the bones of each joint to smoothly move against the other.

Osteoarthritis is probably the most common cause of facet joint pain. This degenerative disease causes progressive cartilage deterioration. Without the spongy cartilaginous cushion, joint bones begin to rub against each other when at rest and during movement causing a substantial amount of pain. Therefore, one option to treat this type of pain is to join rubbing portions of bone together so that this painful friction does not occur.

Present surgical solutions available for facet joint dysfunctions are high-risk, complex and invasive pedicle screw or compression screw based operations associated with prolonged recovery times (such as from about 6 to 24 months; see, e.g., U.S. Pat. No. 6,485,518 and U.S. Pat. No. 6,648,893). The high risk nature of these surgeries leads to uncertain clinical outcomes which can motivate doctors and patients to choose non-surgical symptomatic treatments. While these treatments can help to alleviate back pain temporarily, the underlying cause of the pain continues to progressively worsen. Moreover, there are additional problems associated with screw-based approaches to facet joint fusion. For example, screw-type fixations can work their way loose over time, negating any beneficial effect of the original procedure.

Thus, there is room for great improvement in the surgical treatment of facet joint dysfunction.

SUMMARY OF THE INVENTION

The present invention provides a minimally-invasive procedure and associated surgical tools that can be used to fuse facet joint bones without the use of a screw-based approach. Instead of relying on a screw to hold rubbing facet joints together, the methods of the present invention displaces bone from the facet joint (typically by drilling) and inserts a bone plug into the created hole. The bone plug allows natural bone in-growth into and around the plug such that, typically, a strong and permanent fusion results. The methods of the present invention may be so minimally-invasive that, in some embodiments, it can be practiced arthroscopically or percutaneously. Moreover, in many instances, the procedure can be out-patient.

Specifically, one embodiment according to the present invention includes a method comprising: creating an incision; locating a facet joint with a distal end of a pin wherein the facet joint is formed between two opposing bones and the pin includes a distal end and a proximal end; inserting a spatula; sliding a substantially hollow drill guide over the spatula/pin wherein the drill guide includes a proximal end, a distal end, a handle and a marking wherein the handle is nearer to the proximal end of the drill guide than to the distal end and wherein the distal end includes opposed teeth that can be inserted into the facet joint and wherein the marking indicates the rotational orientation of the two opposed teeth; removing the pin from within the drill guide; inserting a drill bit into the drill guide; drilling a hole into a bone of the facet joint; removing the drill bit; inserting a facet joint bone plug into the hole; and removing the drill guide. In some embodiments, there are two opposed teeth. In some embodiments, the hole is drilled in a manner that permits some of the drilled bone to remain in the drilled hole.

Another embodiment according to the present invention includes a method comprising creating an incision; locating a facet joint with a distal end of a pin wherein the facet joint is formed between two opposing bones and the pin includes a distal end and a proximal end; sliding a substantially hollow spatula over the pin wherein the spatula includes a proximal end, a distal end and a body wherein the distal end includes a planar wedge and the body includes a marking that can indicate the orientation of the planar wedge; adjusting the rotation of the planar wedge until the planar wedge enters the facet joint; sliding a substantially hollow drill guide over the spatula wherein the drill guide includes a proximal end, a distal end, a handle and a marking wherein the handle is nearer to the proximal end of the drill guide than to the distal end, wherein the distal end includes two opposed teeth that can be inserted into the facet joint and the marking indicates the rotational orientation of the two opposed teeth and wherein when the marking on the drill guide is matched or aligned with the marking on the spatula, the orientation of the two opposed teeth is in approximately the same plane defined by the planar wedge; aligning the markings on the spatula and the drill guide; removing the spatula from within the drill guide; inserting a drill bit into the drill guide; drilling a hole into a bone of the facet joint; removing the drill bit; inserting a facet joint bone plug into the hole; removing the drill guide; and closing the incision wherein the pin has also been removed prior to the closing of the incision.

In other embodiments according to the present invention, the inserting of the facet joint bone plug into the hole includes sliding an inserter instrument into the drill guide wherein the inserter instrument has a proximal end and a distal end and a facet joint bone plug associated with the distal end; and disengaging the facet joint bone plug from the distal end of the inserter instrument into the drilled hole.

A particular embodiment according to the present invention includes a method comprising creating an incision; locating a facet joint with a spinal pin; accessing the facet joint with a substantially hollow spatula wherein the spatula includes a proximal end, a distal end, a body and a marking on the body wherein the distal end includes a planar wedge and the accessing includes sliding the substantially hollow spatula over the spinal pin while adjusting the rotation of the planar wedge until the planar wedge enters the facet joint; sliding a substantially hollow drill guide over the spatula wherein the drill guide includes a proximal end, a distal end, a handle and a marking wherein the handle is nearer to the proximal end of the drill guide than to the distal end and wherein the distal end includes two opposed teeth and wherein when the marking on the drill guide is matched or aligned with the marking on the spatula, the orientation of the opposed teeth is in approximately the same plane defined by the planar wedge; matching or aligning the markings on the spatula and the drill guide; removing the spinal pin and the spatula from within the drill guide; inserting a drill bit into the drill guide; drilling a hole into a bone of the facet joint; removing the drill bit; sliding an inserter instrument into the drill guide wherein the inserter instrument has a proximal end and a distal end and a facet joint bone plug associated with the distal end; disengaging the facet joint bone plug from the distal end of the inserter instrument into the drilled hole; and removing the drill guide. In some embodiments, the drilling includes grinding the bone and compacting some of the drilled bone within said hole.

In particular embodiments according to the present invention, the above described methods can further comprise confirming the location of the pin at the facet joint. In one embodiment, the confirming is accomplished with at least one x-ray.

In another embodiment according to the present invention, the method further includes tapping the spatula further into the facet joint following the initial inserting of the planar wedge into the facet joint.

In another embodiment according to the present invention, the method further includes tapping the drill guide following the aligning of the markings so that the opposed teeth of the drill guide engage facet joint bone to secure the orientation of the drill guide until the removing of the drill guide.

In another embodiment according to the present invention, the method further includes tapping the facet joint bone plug into the facet joint following the inserting.

In other embodiments, the present invention includes a method including creating an incision; locating a facet joint with a distal end of a pin wherein the facet joint is formed between two opposing bones and the pin includes the distal end and a proximal end; sliding a substantially hollow drill guide over the pin wherein the drill guide includes a proximal end, a distal end, and a handle wherein the handle is nearer to the proximal end of the drill guide than to the distal end, the distal end includes opposed teeth that can be inserted into the facet joint and; removing the pin from within the drill guide; inserting a drill bit into the drill guide; drilling a hole into a bone of the facet joint; removing the drill bit; inserting a facet joint bone plug into the hole using a bone plug inserter having a raised portion at or near is proximal end, wherein the raised portion prevents over-insertion of the bone plug; and removing the drill guide. In some embodiments, the distal end of the drill guide includes two opposed teeth. In other embodiments, the distal end of the drill guide includes a plurality of teeth, wherein the plurality of teeth includes two opposed teeth and one or more smaller teeth disposed between the two opposed teeth. In some embodiments, the method also includes confirming the location of the pin at the facet joint, for example by taking at least one x-ray. In certain embodiments, the drill guide includes a marking that indicates the rotational orientation of the opposed teeth. In some embodiments, the drilling includes grinding the bone and compacting some of the drilled bone within the hole.

In certain embodiments, the present invention includes a method including: creating an incision; locating a facet joint with a distal end of a pin wherein the facet joint is formed between two opposing bones and the pin includes the distal end and a proximal end; sliding a substantially hollow spatula over the pin wherein the spatula includes a proximal end, a distal end and a body wherein the distal end includes a planar wedge; adjusting the rotation of the planar wedge until the planar wedge enters the facet joint; sliding a substantially hollow drill guide over the spatula wherein the drill guide includes a proximal end, a distal end, and a handle wherein the handle is nearer to the proximal end of the drill guide than to the distal end, the distal end includes opposed teeth that can be inserted into the facet joint; removing the spatula from within the drill guide; inserting a drill bit into the drill guide; drilling a hole into a bone of the facet joint; removing the drill bit; inserting a facet joint bone plug into the hole using a bone plug inserter having a raised portion at or near its proximal end, wherein the raised portion prevents over-insertion of the bone plug; removing the drill guide; and closing the incision wherein the pin has also been removed prior to the closing of the incision. In particular embodiments, the distal end of the drill guide includes two opposed teeth. In certain embodiments, the distal end of the drill guide includes a plurality of teeth, wherein the plurality of teeth includes two opposed teeth and one or more smaller teeth disposed between the two opposed teeth. In some embodiments, the method also includes confirming the location of the pin at the facet joint, including by taking at least one x-ray. In particular embodiments, the body of the spatula includes a marking that can indicate the orientation of the planar wedge. In other embodiments, the spatula further includes a marking and wherein when the marking on the drill guide is matched or aligned with the marking on the spatula, the orientation of the opposed teeth is in approximately the same plane defined by the planar wedge. In some embodiments, the method also includes the step of aligning the markings on the spatula and the drill guide. In some embodiments, the step of inserting the facet joint bone plug into the hole includes sliding an inserter instrument into the drill guide wherein the inserter instrument has a proximal end and a distal end and a facet joint bone plug associated with the distal end; and disengaging the facet joint bone plug from the distal end of the inserter instrument into the drilled hole. In some embodiments, the method also includes tapping the spatula further into the facet joint following the initial inserting of the planar wedge into the facet joint. In some embodiments, the method also includes tapping the drill guide following the aligning of the markings so that the opposed teeth of the drill guide engage facet joint bone to secure the orientation of the drill guide until the removing of the drill guide. In some embodiments, the method also includes tapping the facet joint bone plug into the facet joint following the inserting. In some embodiments, the drilling includes grinding the bone and compacting some of the drilled bone within the hole.

In other embodiments, the present invention includes a method including: creating an incision; locating a facet joint with a spinal pin; accessing the facet joint with a substantially hollow spatula wherein the spatula includes a proximal end, a distal end, and a body wherein the distal end includes a planar wedge and the accessing includes sliding the substantially hollow spatula over the spinal pin while adjusting the rotation of the planar wedge until the planar wedge enters the facet joint; sliding a substantially hollow drill guide over the spatula wherein the drill guide includes a proximal end, a distal end, and a handle wherein the handle is nearer to the proximal end of the drill guide than to the distal end and wherein the distal end includes opposed teeth; removing the spinal pin and the spatula from within the drill guide; inserting a drill bit into the drill guide; drilling a hole into a bone of the facet joint; removing the drill bit; sliding an inserter instrument into the drill guide wherein the inserter instrument has a proximal end and a distal end, wherein a facet joint bone plug is associated with the distal end and wherein the proximal end includes a raised portion that prevents over-insertion of the facet joint bone plug; disengaging the facet joint bone plug from the distal end of the inserter instrument into the drilled hole; and removing the drill guide. In some embodiments, the method also includes confirming the location of the spinal pin at the facet joint, for example by taking at least one x-ray. In other embodiments, the method also includes tapping the spatula further into the facet joint following the initial entry of the planar wedge into the facet joint. In some embodiments, the method also includes tapping the drill guide so that the opposed teeth of the drill guide engage facet joint bone to secure the orientation of the drill guide until the removing of the drill guide. In some embodiments, the method also includes tapping the facet joint bone plug into the hole following the facet joint bone plug's disengagement from the inserter instrument. In some embodiments, the spatula and the drill guide each further includes a marking, wherein when the marking on the drill guide is matched or aligned with the marking on the spatula, the orientation of the opposed teeth is in approximately the same plane defined by the planar wedge. In some embodiments, the method also includes the step of matching or aligning the markings on the spatula and the drill guide. In some embodiments the distal end of the drill guide includes two opposed teeth. In some embodiments, the distal end of the drill guide includes a plurality of teeth, wherein the plurality of teeth includes two opposed teeth and one or more smaller teeth disposed between the two opposed teeth. In some embodiments, the drilling includes grinding the bone and compacting some of the drilled bone within the hole.

The present invention also includes surgical kits. In one embodiment according to the present invention the surgical kit includes a pin comprising a distal end and a proximal end and a substantially hollow drill guide wherein the drill guide includes a proximal end, a distal end, a handle and a marking wherein the handle is nearer to the proximal end of the drill guide than to the distal end and wherein the distal end includes opposed teeth and wherein the marking indicates the rotational orientation of the two opposed teeth. In some embodiments, there are two opposed teeth.

In another embodiment of a surgical kit according to the present invention the surgical kit further includes a bone plug.

An additional embodiment of a surgical kit according to the present invention includes a surgical kit comprising a substantially hollow spatula comprising a proximal end, a distal end, a body and a marking on the body wherein the distal end includes a planar wedge and the marking indicates the rotation of the planar wedge; and a drill guide comprising a proximal end, a distal end, a handle and a marking wherein the handle is nearer to the proximal end of the drill guide than to the distal end and wherein the distal end includes two opposed teeth and wherein when the marking on the drill guide is matched or aligned with the marking on the spatula when the drill guide is place over the spatula, the orientation of the opposed teeth is in approximately the same plane defined by the planar wedge.

Surgical kit embodiments according to the present invention can further comprise a tool selected from the group consisting of an inserter instrument, a spinal pin, a spinal needle, an impacter, a hammer, a drill bit, a drill, a reamer, a dilator, a bone plug holder, a bone plug, and an autoclavable surgical tool kit box.

One particular surgical kit according to the present invention includes a surgical kit comprising a substantially hollow spatula comprising a proximal end, a distal end, a body and wherein the distal end includes a planar wedge; and a drill guide comprising a proximal end, a distal end, and a handle wherein the handle is nearer to the proximal end of the drill guide than to the distal end and wherein the distal end includes opposed teeth. In some embodiments, the substantially hollow spatula includes a marking on the body. In some embodiments, the marking on the body of the spatula indicates the rotation of the planar wedge. In some embodiments, the distal end of the drill guide includes two opposed teeth. In some embodiments the drill guide includes a marking. In some such embodiments, the when the marking on the drill guide is matched or aligned with the marking on the spatula when the drill guide is place over the spatula, the orientation of the opposed teeth is in approximately the same plane defined by the planar wedge Additional embodiments of kits according to the present invention can also individually, collectively or in various combinations include one or more of a spinal pin, a spinal needle, an impacter, a hammer, a reamer, a drill bit, a reamer, a drill, a dilator, a dilator tube, a guide wire, a bone plug, and a bone plug holder wherein all components of the kit except for the reamer can be re-used, stored and sterilized in a single autoclavable surgical tool kit box.

In some embodiments the present invention includes a surgical kit including a substantially hollow spatula comprising a proximal end, a distal end, and a body wherein the distal end includes a planar wedge; and a drill guide comprising a proximal end, a distal end, and a handle wherein the handle is nearer to the proximal end of the drill guide than to the distal end and wherein the distal end includes opposed teeth; a spinal pin; a drill bit; a bone plug inserter comprising a proximal end and a distal end, wherein the distal end is configured to interact with a bone plug and wherein the proximal end includes a raised portion that prevents over-insertion of the bone plug; a bone plug holder; and wherein all components of the kit can be stored and sterilized in a single autoclavable tool box. In certain embodiments, the spatula and the drill guide each further includes a marking, wherein when the marking on the drill guide is matched or aligned with the marking on the spatula, the orientation of the opposed teeth is in approximately the same plane defined by the planar wedge. In particular embodiments, the marking on the spatula indicates the rotation of the planar wedge. In other embodiments, the surgical tool kit also includes a spinal needle, an impacter, a hammer, a drill, a reamer, a dilator or a bone plug. In some embodiments the drill bit is configured to grind the bone and compact some of the drilled bone within the hole.

In some embodiments, the present invention includes a method including: creating an incision; locating a facet joint with a distal end of a pin wherein the facet joint is formed between two opposing bones and the pin comprises the distal end and a proximal end; sliding a substantially hollow drill guide over the pin wherein the drill guide comprises a proximal end, a distal end, and a handle wherein the handle is nearer to the proximal end of the drill guide than to the distal end, the distal end comprises opposed teeth with a length longer than about 3 mm that can be inserted into the facet joint; removing the pin from within the drill guide; inserting a drill bit into the drill guide; drilling a hole into a bone of the facet joint; removing the drill bit; inserting a facet joint bone plug into the hole using a bone plug inserter having a raised portion at or near is proximal end, wherein the raised portion prevents over-insertion of the bone plug; and removing the drill guide. The opposed teeth may be about 3 mm to about 20 mm in length. In one example, the opposed teeth are about 10 mm in length.

In some embodiments, opposed teeth comprise one or more selected from the group consisting of a straight portion and a tapered portion. In one example, the straight portion is about 2 mm to about 10 mm in width. For example, the straight portion may be about 3 mm in width.

The tapered portion may taper at an angle between about 1 degree to just under about 90 degrees. In one example, the taper is about an angle of 45 degrees. Further, the tapered portion may taper from a starting width of about 3 mm to a range from just below a width of 3 mm to a width of about 0.1 mm. The tapered portion may comprise more than one taper.

The opposed teeth may comprise at the distal end of the teeth, one or more selected from the group consisting of a flat edge, a sharp point and a rounded off edge. The teeth may comprise a straight portion and a tapered portion. The straight portion may be about 3 mm in length and at the proximal end of the teeth, and the tapered portion may be about 7 mm in length and at the distal end of the teeth. Further, the distal end of the drill guide may comprise a plurality of teeth. The plurality of teeth may comprise two opposed teeth and one or more smaller teeth disposed between the two opposed teeth.

In some embodiments, one of the opposed teeth may comprise a straight portion with a first end and a second end, a tapered portion with a first end and a second end, and an angled portion with a first end and a flat second end. The first end of the tapered portion may be disposed at the second end of the straight portion. The first end of the angled portion may be disposed at the second end of the straight portion. The straight portion may be about 3 mm in length and about 3 mm in width. The tapered portion and the angled portion, together, may be about 7 mm in length. Further, the tapered portion may comprise a slight taper from the first end of the tapered portion to the second end of the tapered portion until the tapered portion is about 2.25 mm in width. The angled portion may comprise a second taper at an angle of about 45 degrees, thereby providing a more extreme narrowing at the flat second end of the angled portion.

In various embodiments, the present invention includes a method including creating an incision locating a facet joint with a distal end of a pin wherein the facet joint is formed between two opposing bones and the pin comprises the distal end and a proximal end; sliding a substantially hollow spatula over the pin wherein the spatula comprises a proximal end, a distal end and a body wherein the distal end comprises a planar wedge, and the body comprises a longitudinal marking that can indicate the orientation of the planar wedge and one or more transverse guide markings near the proximal end of the spatula; adjusting the rotation of the planar wedge until the planar wedge enters the facet joint; sliding a substantially hollow drill guide over the spatula wherein the drill guide comprises a proximal end, a distal end, and a handle wherein the handle is nearer to the proximal end of the drill guide than to the distal end, the distal end comprises two opposed teeth that can be inserted into the facet joint and a marking on the proximal end that can be aligned with the longitudinal marking on the spatula thereby allowing the orientation of the opposed teeth to be in approximately the same plane defined by the planar wedge; inserting the drill guide into the incision until the proximal end of the drill guide aligns with the first transverse guide mark on the spatula; aligning the longitudinal marking on the spatula with the marking on the drill guide thereby aligning the opposed teeth in approximately the same plane defined by the planar wedge; further inserting the drill guide into the incision and using the one or more transverse guide markings to indicate the depth of the insertion of the teeth of the drill guide into the facet joint; removing the spatula from within the drill guide; inserting a drill bit into the drill guide; drilling a hole into a bone of the facet joint; removing the drill bit; inserting a facet joint bone plug into the hole using a bone plug inserter having a raised portion at or near its proximal end, wherein the raised portion prevents over-insertion of the bone plug; and removing the drill guide.

The spatula may comprise between one transverse guide mark to five transverse guide marks. In one example, the spatula comprises three transverse guide marks. The transverse guide marks may be equidistant from each other. In one example, the transverse guide marks are about 1 mm to about 20 mm apart from each other. In another example, the transverse guide marks are about 10 mm apart from each other. The first transverse guide mark may be near the proximal end of the spatula. The second transverse guide mark may be further from the proximal end of the spatula than the first transverse guide mark. The third transverse guide mark may be further from the proximal end of the spatula than the second transverse guide mark.

In some embodiments, the step of inserting the drill guide into the incision further comprises inserting the drill guide into the incision until the proximal end of the drill guide aligns with the first transverse guide mark on the spatula; aligning the longitudinal marking on the spatula with the marking on the drill guide thereby aligning the opposed teeth in approximately the same plane defined by the planar wedge; further inserting the drill guide into the incision until the proximal end of the drill guide aligns with the second transverse guide mark on the spatula, thereby indicating that the distal end of the drill guide is at the entry level of the facet joint or closely approaching it; further aligning the longitudinal marking on the spatula with the marking on the drill guide thereby assuring the opposed teeth are in approximately the the plane defined by the planar wedge; and further inserting the drill guide into the incision until the proximal end of the drill guide aligns with the third transverse guide mark on the spatula, thereby indicating that the opposed teeth are fully inserted or approximately fully inserted into the facet joint.

In some embodiments, the present invention includes a method including creating an incision; locating a facet joint with a distal end of a pin wherein the facet joint is formed between two opposing bones and the pin comprises the distal end and a proximal end; sliding a substantially hollow spatula over the pin wherein the spatula comprises a proximal end, a distal end and a body wherein the distal end comprises a planar wedge, and the body comprises a longitudinal marking that can indicate the orientation of the planar wedge, and one or more transverse guide markings near the proximal end of the spatula; adjusting the rotation of the planar wedge until the planar wedge enters the facet joint; sliding a substantially hollow drill guide over the spatula wherein the drill guide comprises a proximal end, a distal end wherein the distal end comprises opposed teeth with a length longer than about 3 mm that can be inserted into the facet joint, a handle wherein the handle is nearer to the proximal end of the drill guide than to the distal end, and a marking on the proximal end that can be aligned with the longitudinal marking on the spatula thereby allowing the orientation of the opposed teeth to be in approximately the same plane defined by the planar wedge, and; inserting the drill guide into the incision until the proximal end of the drill guide aligns with the first transverse guide mark on the spatula; aligning the longitudinal marking on the spatula with the marking on the drill guide thereby aligning the opposed teeth in approximately the same plane defined by the planar wedge; further inserting the drill guide into the incision until the proximal end of the drill guide aligns with the second transverse guide mark on the spatula, thereby indicating that the distal end of the drill guide is at the entry level of the facet joint or closely approaching it; further aligning the longitudinal marking on the spatula with the marking on the drill guide thereby assuring the opposed teeth are in approximately the same plane defined by the planar wedge; further inserting the drill guide into the incision and using the one or more transverse guide markings to indicate the depth of the insertion of the teeth of the drill guide into the facet joint; removing the spatula from within the drill guide; inserting a drill bit into the drill guide; drilling a hole into a bone of the facet joint; removing the drill bit; inserting a facet joint bone plug into the hole using a bone plug inserter having a raised portion at or near its proximal end, wherein the raised portion prevents over-insertion of the bone plug; and; removing the drill guide; and closing the incision wherein the pin has also been removed prior to the closing of the incision.

The opposed teeth may be a length of about 10 mm. The opposed teeth may comprise a straight portion and a tapered portion wherein the straight portion is about 3 mm in length and at the proximal end of the teeth, and the tapered portion is about 7 mm in length and at the distal end of the teeth.

In some embodiments, one of the opposed teeth comprises a straight portion with a first end and a second end, a tapered portion with a first end and a second end, and an angled portion with a first end and a flat second end. The first end of the tapered portion may be disposed at the second end of the straight portion. The first end of the angled portion may be disposed at the second end of the tapered portion. The straight portion may be about 3 mm in length and about 3 mm in width. The tapered portion and the angled portion, together, may be about 7 mm in length. The tapered portion may comprise a slight taper from the first end of the tapered portion to the second end of the tapered portion until the tapered portion is about 2.25 mm in width. The angled portion may comprise a second taper at an angle of about 45 degrees thereby providing a more extreme narrowing at the flat end of the angled portion.

In some embodiments, the spatula comprises three transverse guide marks. The transverse guide marks may be about 10 mm apart from each other. The first transverse guide mark may be near the proximal end of the spatula. The second transverse guide mark may be further from the proximal end of the spatula than the first transverse guide mark. The third transverse guide mark may be further from the proximal end of the spatula than the second transverse guide mark.

The step of inserting the drill guide into the incision may further comprise inserting the drill guide into the incision until the proximal end of the drill guide aligns with the first transverse guide mark on the spatula; aligning the longitudinal marking on the spatula with the marking on the drill guide thereby aligning the opposed teeth in approximately the same plane defined by the planar wedge; further inserting the drill guide into the incision until the proximal end of the drill guide aligns with the second transverse guide mark on the spatula, thereby indicating that the distal end of the drill guide is at the entry level of the facet joint or closely approaching it; further aligning the longitudinal marking on the spatula with the marking on the drill guide thereby assuring the opposed teeth are in approximately the same plane defined by the planar wedge; and further inserting the drill guide into the incision until the proximal end of the drill guide aligns with the third transverse guide mark on the spatula, thereby indicating that the opposed teeth are fully inserted or approximately fully inserted into the facet joint.

The plurality of teeth may comprise two opposed teeth and one or more smaller teeth disposed between the two opposed teeth. Inserting of the facet joint bone plug into the hole may comprise sliding an inserter instrument into the drill guide wherein the inserter instrument has a proximal end and a distal end and a facet joint bone plug associated with the distal end; and disengaging the facet joint bone plug from the distal end of the inserter instrument into the drilled hole.

The method may further comprise tapping the spatula further into the facet joint following the initial inserting of the planar wedge into the facet joint. The method may further comprise tapping the drill guide following the aligning of the markings so that the opposed teeth of the drill guide engage facet joint bone to secure the orientation of the drill guide until the removing of the drill guide. The method may further comprise tapping the facet joint bone plug into the facet joint following the inserting.

In some embodiments, the present invention includes a surgical kit including a substantially hollow spatula comprising a proximal end, a distal end, and a body wherein the distal end comprises a planar wedge, the substantially hollow spatula comprising a guide mark; a drill guide comprising a proximal end, a distal end, and a handle wherein the handle is nearer to the proximal end of the drill guide than to the distal end and wherein the distal end comprises opposed teeth with a length longer than about 3 mm; a spinal pin; a drill bit; a bone plug inserter comprising a proximal end and a distal end, wherein the distal end is configured to interact with a bone plug and wherein the proximal end comprises a raised portion that prevents over-insertion of the bone plug; a bone plug holder; and wherein all components of the kit can be stored and sterilized in a single autoclavable tool box.

The spatula and the drill guide may each further comprises a marking, wherein when the marking on the drill guide is matched or aligned with the marking on the spatula. The orientation of the opposed teeth may be in approximately the same plane defined by the planar wedge. The marking on the spatula indicates the rotation of the planar wedge.

The surgical kit may further comprise one or more tools selected from the group consisting of a spinal needle, an impacter, a hammer, a drill, a reamer, a dilator and a bone plug. In another example, the surgical kit further comprises a bone plug. The drill bit may be configured to grind the bone and compact some of the drilled bone within the hole. In another example, the spatula comprises one or more transverse guide markings. In yet another example, the spatula comprises three transverse guide markings.

The methods and surgical kits of the present invention described above can also be used or sold in conjunction with bone plugs according to the present invention. In one embodiment along the length of the bone plug there is at least one major diameter and at least one minor diameter. In another embodiment the bone plug includes a fin or a series of fins. In some embodiments, the fins in the series are spaced approximately 1 mm apart.

BRIEF DESCRIPTION OF THE DRAWINGS

FIGS. 6-8 show the insertion of a spatula with a planar distal tip into the facet joint.

FIG. 13 shows an enlarged view the distal tip of a bone plug inserter with a bone plug ready for deployment.

FIG. 14 shows the bone plug inserter of FIG. 13 ready for insertion through the drill guide.

FIG. 15 represents the tamping or hammering of the proximal end of the inserter once inserted through the drill guide.

FIG. 20 shows an alternative representation of a hole prepared for insertion with a bone plug oriented for insertion into the hole.

FIG. 21 shows a frustum shaped bone plug of the present invention that can be used in facet joint fusion.

FIG. 22 shows a bone plug inserted in the hole of FIG. 20 with an application tube for inserting synthetic or biologic material into the facet joint.

FIGS. 45-50 show alternative designs of the handle of the drill guide, wherein FIGS. 48 and 49 show a front view and a side view of the same handle.

DETAILED DESCRIPTION OF THE INVENTION

Figure 1:
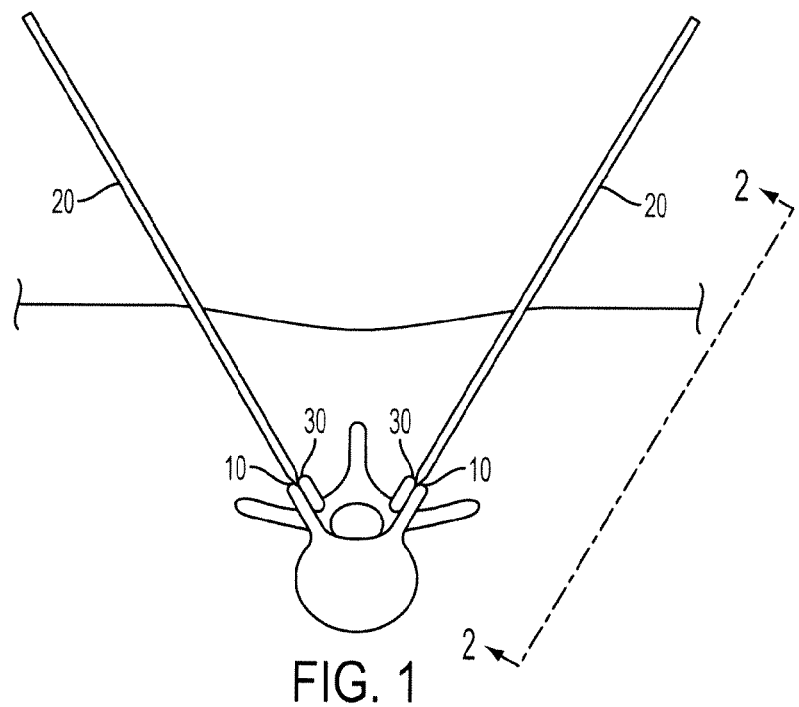
FIG. 1 shows facet joint location with surgical pins.

It is understood that the present invention is not limited to the particular methodologies, protocols, systems and methods, etc., described herein, as these may vary. It is also to be understood that the terminology used herein is used for describing particular embodiments only, and is not intended to limit the scope of the present invention. It must be noted that as used herein and in the appended claims, the singular forms "a," "an," and "the" include the plural reference unless the context clearly dictates otherwise. For instance, a reference to a surgical kit refers to one or more surgical kits and a reference to "a method" is a reference to one or more methods and includes equivalents thereof known to those of ordinary skill in the art and so forth.

Unless defined otherwise, all technical and scientific terms used herein have the same meanings as commonly understood by one of ordinary skill in the art to which this invention belongs. Specific methods, devices, systems and materials are described, although any methods and materials similar or equivalent to those described herein can be used in the practice or testing of the present invention.

Back pain is a prevalent problem in the United States. One root cause of back pain, particularly the persistent and disabling kind, is problems with facet joints. Each vertebra has two sets of facet joints. One pair faces upward and the other pair faces downward. Within each set there is a facet joint on the left side of each vertebra and a facet joint on the right side of each vertebra.

Facet joints, also called zygapophyseal or apophyseal joints are the system of joints that allow movement (forward bending, backward bending and twisting) of the spine. While these joints allow movement of the spine, their interlocking nature also helps to stabilize the spine.

Similar to other joints in the body, each facet joint is surrounded by a capsule of connective tissue and produces synovial fluid to nourish and lubricate the joint. The joint surfaces themselves are coated with a thick spongy material called articular cartilage that enables the bones of each joint to smoothly move against the other.

Osteoarthritis is one cause of facet joint pain. This degenerative disease causes progressive cartilage deterioration. Without the spongy cartilaginous cushion, joint bones rub against each other when at rest and during movement causing a substantial amount of pain. Therefore, one option to treat this type of pain is to join rubbing portions of bone together so that this painful friction does not occur.

The present invention provides a minimally-invasive surgical option and associated tools to fuse facet joints for the treatment of back pain. The methods and tools can be used to perform the joint fusion in a minimally invasive procedure, utilizing a small incision hence requiring a minimal number of sutures, for example arthroscopically or percutaneously, in some instances, leading to an out-patient procedure. In one embodiment, the methods and tools can be used to fuse the forty-eight spinal facet joints on the spine from C1-C2 through L5-S1.

Figure 34:
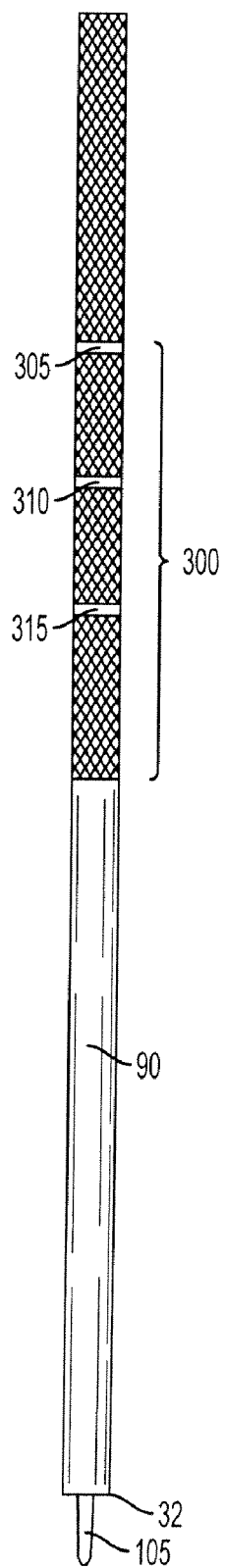
FIG. 34 shows an enlarged view of the spatula.

Turning to the figures, in a specific embodiment, a spatula 90 as depicted in FIG. 34 may be utilized in the present invention for insertion into the facet joint as depicted in FIGS. 6-8. The spatula 90 may be substantially hollow, wherein the distal end of the spatula 90 can have a planar wedge 105. In another embodiment, and as depicted in FIGS. 6 and 7, the spatula 90 may also have a marking aligned with the longitudinal axis of the spatula 115 that can indicate the orientation of the planar wedge once the spatula is inserted into the facet joint. As depicted in FIG. 34, the spatula 90 may also have one or more additional markings for guidance aligned with the transverse axis of the spatula 300. In a specific embodiment, and as shown in FIG. 34, the spatula 90 may have three transverse guide markings indicated as 305, 310 and 315. In alternative embodiments, the spatula 90 may have one or more transverse guide markings, two transverse guide markings, three transverse guide markings, four transverse guide markings and five transverse guide markings. In another embodiment, the transverse guide markings may be equidistant from each other. In another specific embodiment, the transverse guide markings may be about 1 mm to about 20 mm apart from each other. In another specific embodiment, the transverse guide markings may be about 10 mm apart from each other. In another specific embodiment, the transverse guide markings may be less than about 10 mm apart from each other. In another specific embodiment, the transverse guide markings may be more than about 10 mm apart from each other.

In another embodiment, the transverse guide markings may be laser etched or marked. In another embodiment, the transverse guide markings may be marked 360 degrees around the circumference of the spatula. In another embodiment, the markings may be less than about 1 mm wide. In another embodiment, the markings, may be more than about 1 mm wide. In another embodiment, the markings, may be about 1 mm wide. In another embodiment, the proximal end of the spatula may have knurling as depicted in FIG. 34, or other appropriate scoring to, for example, assist in gripping the spatula.

Figure 35:
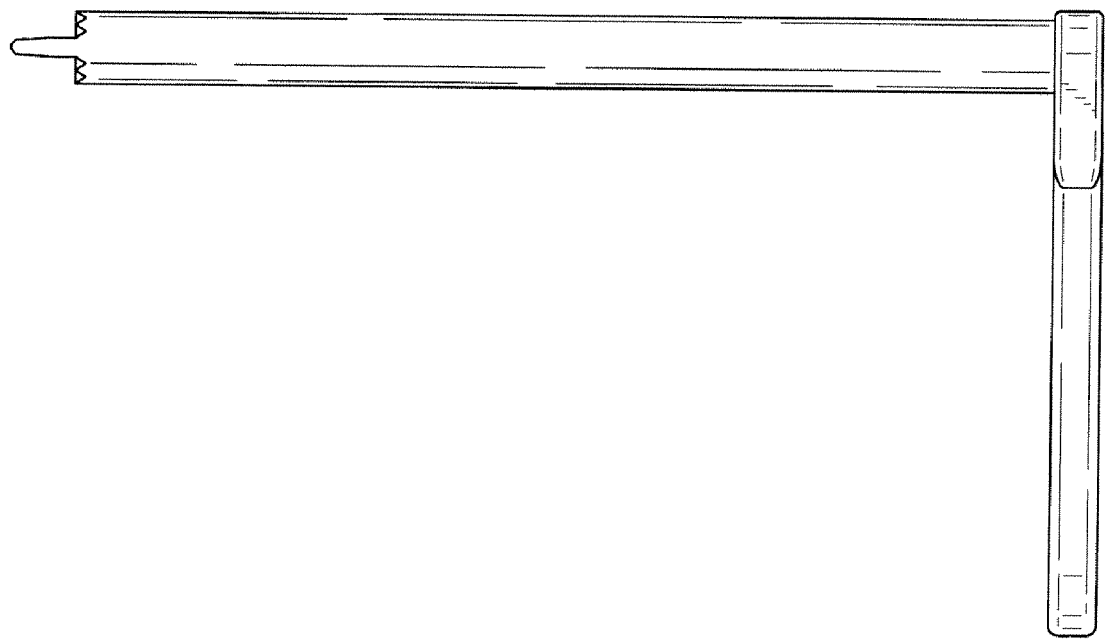
FIGS. 35-36 show the side view of two alternative designs of the drill guide.
Figure 36:
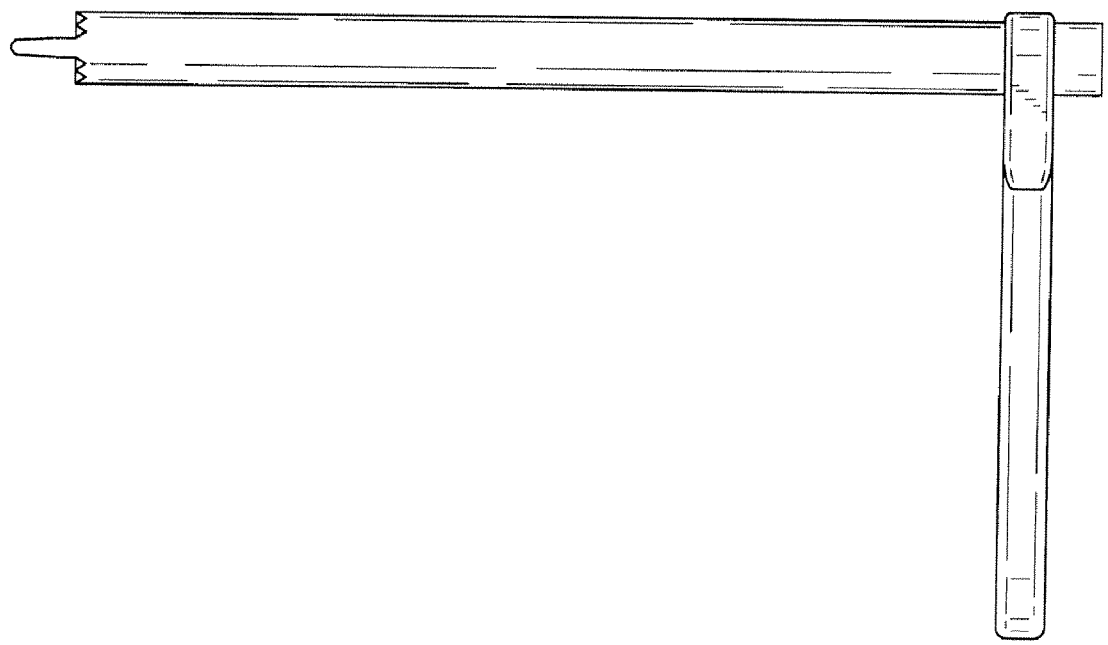
Figure 37:
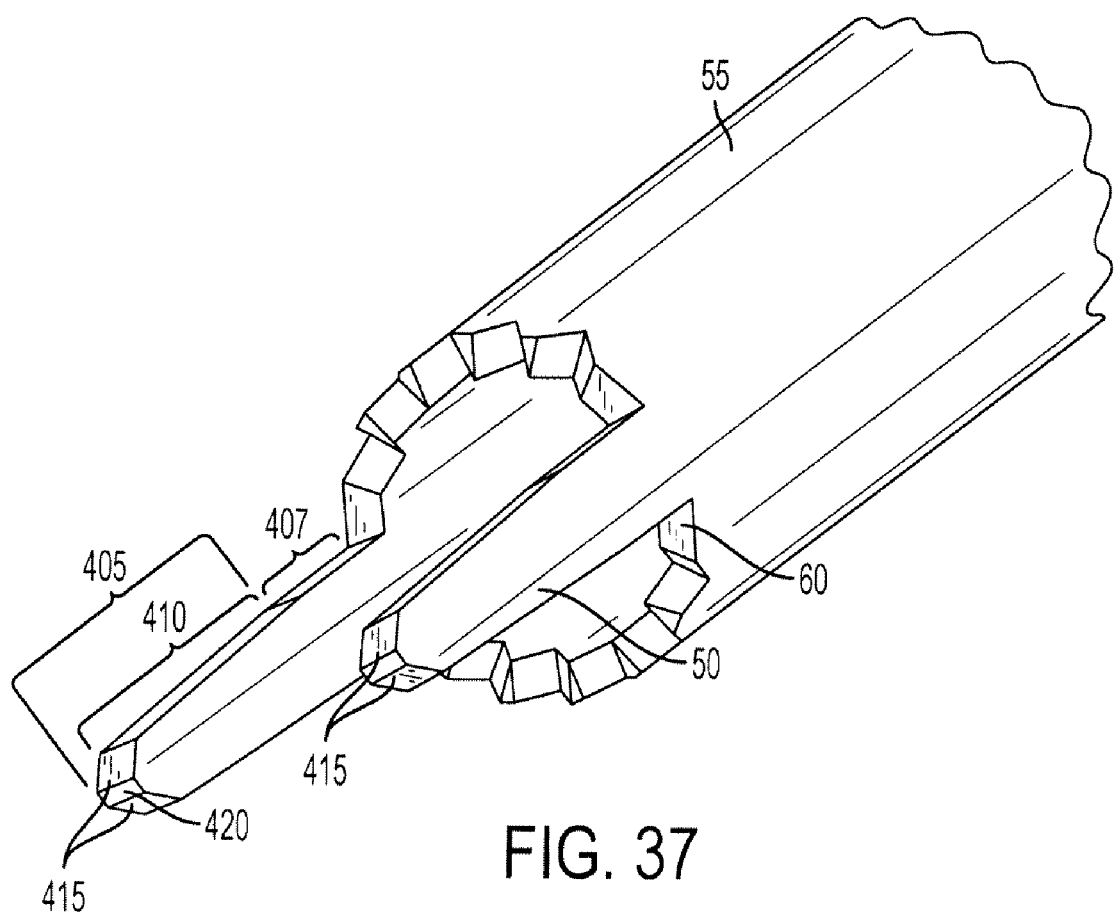
FIG. 37 shows an enlarged view of the two large teeth of the drill guide as depicted in FIGS. 35-36.
Figure 38:
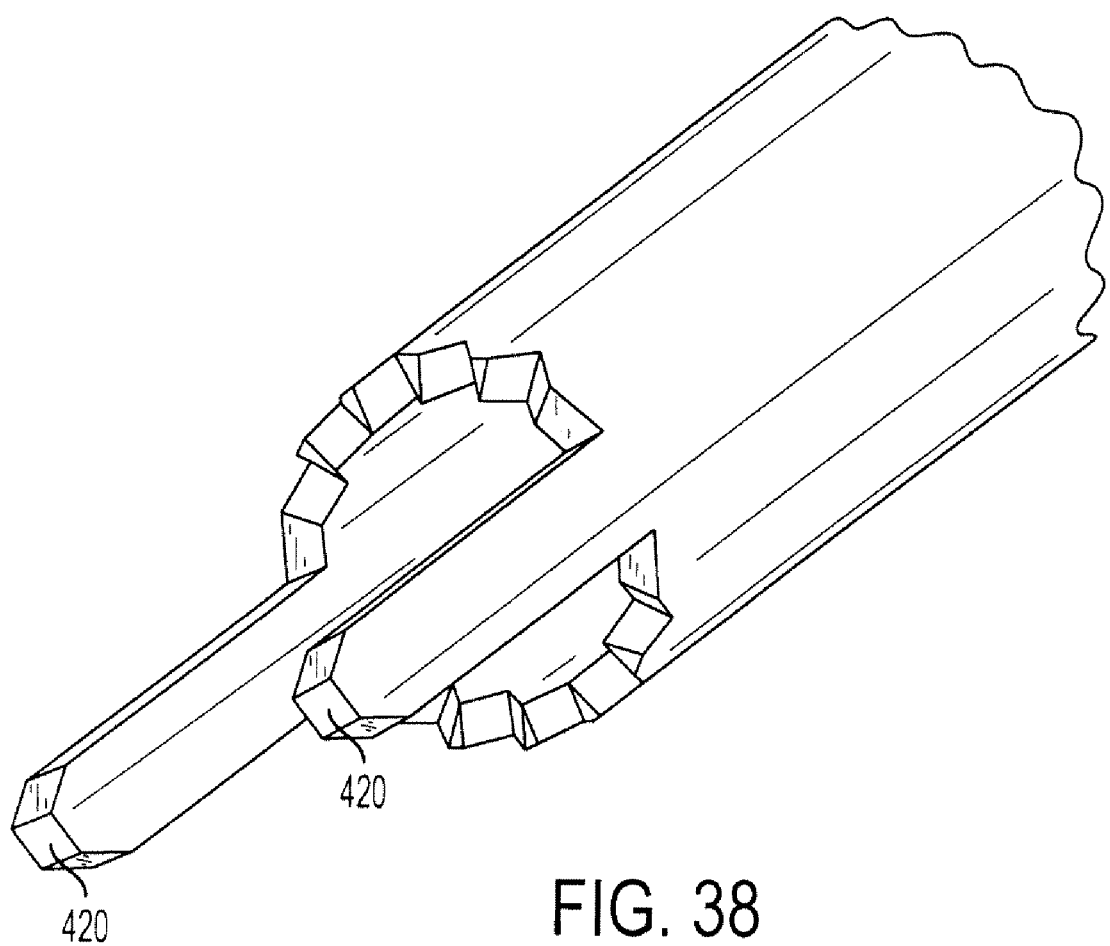
FIGS. 38-43 show alternative designs of the teeth of the drill guide.

FIGS. 35 and 36 depict a specific embodiment of a substantially hollow drill guide that can be slid, for example, over a pin and a spatula in the surgical techniques of the present invention. FIG. 37 depicts an enlarged view of the distal end of the drill guides from FIGS. 35 and 36. The distal end of the drill guide can have one or more teeth 50. In certain embodiments, the distal end of the drill guide has two larger opposed teeth 50 that are separated by about 180 degrees around the circumference of the distal end of the drill guide. In certain embodiments, the drill guide can have a marking that indicates the rotational orientation of the two large teeth 50. One or more smaller teeth 60 may also be found between or surrounding the opposed teeth 50.

Figure 9:
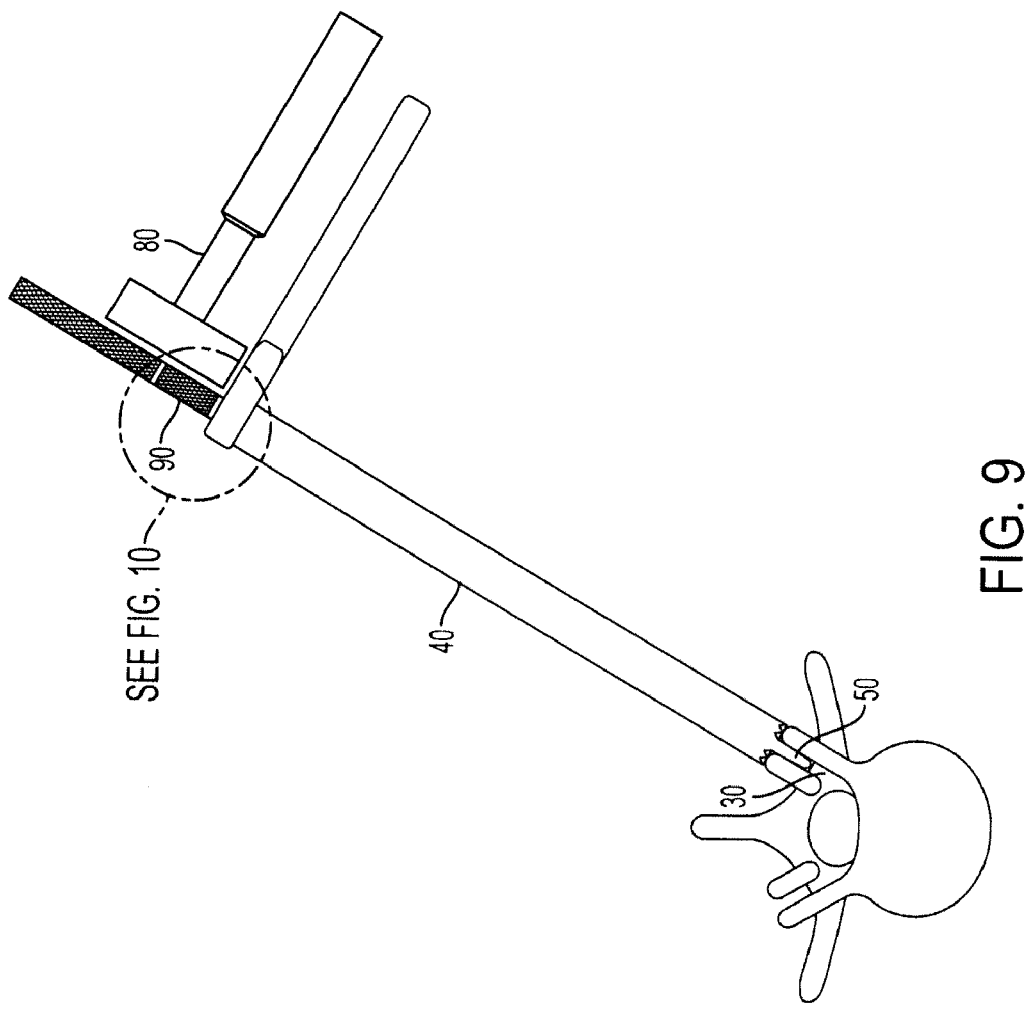
FIG. 9 depicts insertion of the drill guide over the spatula.

With respect to the large opposed teeth, and as depicted in FIG. 37, the two large opposed teeth 50 may be extended in length with respect to the barrel 55 of the drill guide. Extending the length of the large opposed teeth 50 allows for a further insertion into the facet joint, thus providing more stability of the drill guide 40 in the facet joint 30, as depicted in FIG. 9. The stability of the drill guide therefore allows for a more stable and accurate procedure to be performed, including a more accurate and stable drilling into the facet joint, as well as a more accurate and stable insertion, placement and fixation of the bone plug into the facet joint 30. By way of example, FIG. 37 depicts longer large opposed teeth 50 which, in the specific depicted embodiment, are about 10 mm in length. FIG. 37 further depicts longer large teeth 50 as opposed to the shorter large teeth depicted in FIG. 42. In one specific embodiment, the two large teeth 50 may be more than about 3 mm in length. In a specific embodiment, the two large teeth 50 may be about 3 mm in length to about 20 mm in length. In a specific embodiment, and as depicted in FIG. 37, the two large teeth may be about 10 mm in length. In a particular embodiment the length of the two large opposed teeth may be about 3 mm long, about 4 mm long, about 5 mm long, about 6 mm long, about 7 mm long, about 8 mm long, 9 mm long, about 10 mm long, about 11 mm long, about 12 mm long, about 13 mm long, about 14 mm long, about 15 mm long, about 16 mm long, about 17 mm long, about 18 mm long, about 19 mm long and about 20 mm long. In a particular embodiment the length of the two large opposed teeth may be over 20 mm long.

In other embodiment of the present invention, the opposed teeth 50 may encompass various shapes and sizes. In a specific embodiment, the opposed teeth 50 may be straight. In another specific embodiment, the opposed teeth 50 may be tapered.

In another specific embodiment, and as depicted in FIG. 37, one or both of the opposed teeth 50 may contain a straight portion 407, a tapered portion 410, and an angled portion 415.

Regarding the straight portion 407 of one of the opposed teeth 50, as shown in FIG. 37, the straight portion 407 may be about 3 mm in length. In an alternative embodiment, the straight portion 407 may be more than about 3 mm to about 20 mm in length. In a specific embodiments, the straight portion may be about 4 mm in length, about 5 mm in length, about 6 mm in length, about 7 mm in length, about 8 mm in length, about 9 mm in length, about 10 mm in length, about 11 mm in length, about 12 mm in length, about 13 mm in length, about 14 mm in length, about 15 mm in length, about 16 mm in length, about 17 mm in length, about 18 mm in length, about 19 mm in length or about 20 mm in length.

Regarding the tapered portion 410 of one of the opposed teeth 50 as depicted in FIG. 37, the tapered portion 410 and the angled portion 415, together, have a length 405 that may be about 7 mm in length. In alternative embodiments, the length 405 of the tapered portion 410 and the angled portion 415, together, of one of the opposed teeth 50 may be about 1 mm in length to about 20 mm in length. In other embodiments, the length 405 of the tapered portion 410 and the angled portion 415, together, of one of the opposed teeth 50 may be about 1 mm in length, about 2 mm in length, about 3 mm in length, about 4 mm in length, about 5 mm in length, about 6 mm in length, about 7 mm in length, about 8 mm in length, about 9 mm in length, about 10 mm in length, about 11 mm in length, about 12 mm in length, about 13 mm in length, about 14 mm in length, about 15 mm in length, about 16 mm in length, about 17 mm in length, about 18 mm in length, about 19 mm in length, or about 20 mm in length.

In a specific embodiment, as shown in FIG. 37, each of the opposed teeth 50 may have a straight portion 407 of about 3 mm in length and a tapered portion 410 and an angled portion 415, together, of about 7 mm in length. In another specific embodiment, and as shown in FIG. 37, the straight portion 407 may have a first end and a second end, the tapered portion 410 may have a first end and a second end, and the angled portion 415 may have a first end and a flat second end 420. The first end of the straight portion 407 may be disposed at the barrel 55. The first end of the tapered portion 410 may be disposed at the second end of the straight portion 407. The first end of the angled portion 415 may be disposed at the second end of the tapered portion 410.

In another specific embodiment, the opposed teeth 50 may each have one or more tapers to provide easier insertion into the facet joint. In this context a "taper" refers to a distinct gradient of tapering. As such, an embodiment having a plurality of tapers means the embodiment tapers at a plurality of gradients. In another specific embodiment, the opposed teeth 50 may each have one taper. FIGS. 38-41 each depict different designs of opposed teeth each with one taper. In another specific embodiment, the opposed teeth may each have two tapers. FIG. 37 depicts opposed teeth 50 each with two tapers. In an alternative embodiment of the present invention, the opposed teeth may each have three tapers. In another specific embodiment, the opposed teeth may each have four tapers. In another specific embodiment, the opposed teeth may each have five tapers or more.

Figure 39:
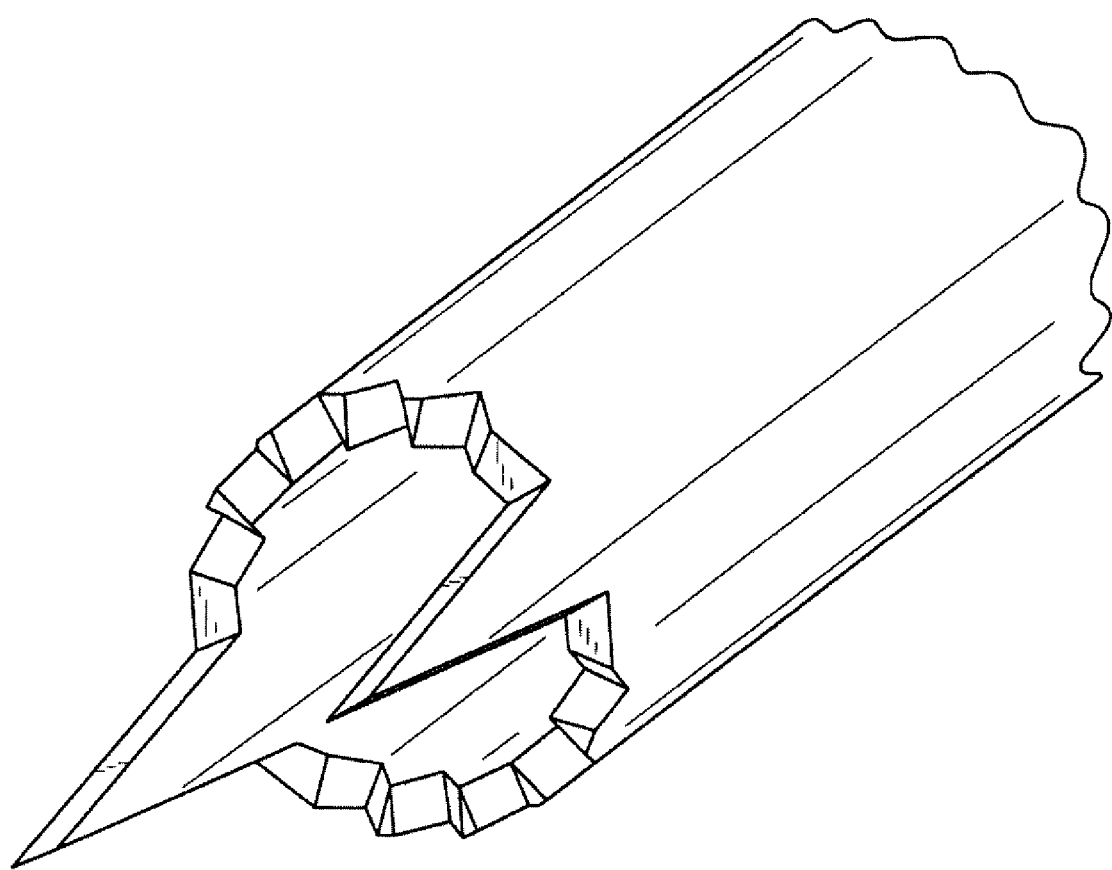

In another specific embodiment, each of the opposed teeth may only have a straight portion. In another embodiment, each of the opposed teeth may have only a tapered portion. Such an embodiment is depicted in FIG. 39, wherein the tapered portion begins tapering directly from the barrel of the drill guide.

In another specific embodiment, the opposed teeth may each have a straight portion and more than one taper. A specific embodiment of a two tapered system including a straight portion 407 of one of the opposed teeth 50 is depicted in detail in FIG. 37. Specifically, the straight portion 407 located on the first end of one of the opposed teeth 50 extends out from the end of the barrel 55 of the drill guide. Moving towards the angled portion 415, a slight first taper of the tapered portion extends from the second end of the straight portion 407. Moving further towards the flat second end 420 of the angled portion 415, a second taper extends from the second end of the tapered portion 410.

Various taper gradients relative to the straight portion of one of the opposed teeth may be encompassed in the present invention. If either of the opposed teeth do not contain a straight portion, various taper gradients relative to the barrel 55 of the drill guide may also be encompassed in the present invention. In a specific embodiment, each of the opposed teeth may be tapered with about a 1 degree gradient and thus creating a slight taper. In another embodiment, the taper gradient may be just under about 90 degrees. In another embodiment, the taper gradient may from about 1 degree to about just under 90 degrees. In another embodiment, the taper gradient may be about 45 degrees. In another embodiment, each of the opposed teeth 50 may have more than one taper at different taper gradients. In other embodiments, the taper gradient may be about 1 degree, about 5 degrees, about 10 degrees, about 15 degrees, about 20 degrees, about 25 degrees, about 30 degrees, about 35 degrees, about 40 degrees, about 50 degrees, about 55 degrees about 60 degrees, about 65 degrees, about 70 degrees, about 75 degrees, about 80 degrees, or about 85 degrees.

Again referring to FIG. 37, is a depiction of two tapers at different taper gradients. As shown, the first taper of the tapered portion 410 is at a slight taper relative to the straight portion 407. The second taper of the angled portion 415, however, provides a larger taper gradients. Specifically, as depicted in FIG. 37, the second taper of the angled portion 415 is angled 45 degrees (a taper gradient of 45 degrees) relative to the straight portion 407, and thus provides a more extreme narrowing at the second flat end 420 of the angled portion 415.

The taper gradient(s), thus may also affect the width of each of the opposed teeth throughout each tooth's length. In a specific embodiment, and as depicted in FIG. 37, the width of each of the opposed teeth at the straight portion 407 is about 3 mm. Because of the first taper of the tapered portion 410, the width of each of the opposed teeth begins to narrow gradually. At the second end of the tapered portion 410 which is disposed at the first end of the angled portion 415, the width of each of the opposed teeth 50 is about 2.25 mm. At the angled portion 415, the width of each of the opposed teeth 50 is more drastically reduced. In a specific embodiment, the straight portion 407 may have a width of about 3 mm and the second end of the tapered portion 410 disposed at the angled portion 415 may have a width of about 2.25 mm. In an alternative embodiment, the width of the straight portion 407 may be more than about 3 mm. In another embodiment, the width of straight portion 407 may be about 10 mm. In another embodiment, the width of the straight portion 407 and the tapered portion 410 may be from about 10 mm to about 0.1 mm anywhere along the length of each of the opposed teeth 50.

In yet another embodiment, the width of the straight portion 407 may about 3 mm and the length of the opposed teeth 50 may be about 10 mm. In another embodiment, the width of the straight portion 407 may about 3 mm and the length of the opposed teeth 50 may be about 10 mm, wherein the straight portion is about 3 mm in length. Such embodiments provide numerous advantages. First, the longer length of the opposed teeth at 10 mm, as opposed to, for example, 3 mm, allows for a further insertion of the opposed teeth 50 into the facet joint, thus providing more stability of the drill guide 40 in the facet joint 30, as depicted in FIG. 9. The stability of the drill guide therefore allows for a more stable and accurate procedure to be performed, including a more accurate and stable drilling into the facet joint and insertion, placement and fixation of the bone plug into the facet joint 30. The 3 mm length in width of the opposable teeth also aides in the insertion of the bone plug. The 3 mm width of the straight portion enters into the facet joint 30, therefore expanding the gap of the facet joint. This expansion therefore allows for easier insertion of the bone plug into the facet joint 30. Further, after the drill guide 40 is removed from the facet joint after implanting the drill guide, the facet joint may contract and allow the bone plug to sit more secured in the facet joint.

The taper gradient of the tapered portion 410 may also affect the width of the angled portion 415 including the flat second end 420 of the angled portion 415. For example, because of the taper of the tapered portion 410 and the taper of the angled portion 415 in FIG. 37, the width at the flat second end 420 of the angled portion 415 is smaller than the width of the flat second end 420 in FIG. 38, where only one taper exists. In a specific embodiment, the width of the flat second end 420 may be about 10 mm to about 0.1 mm. Specifically, and as provided in FIGS. 38 and 39, the end of each of the opposed teeth, which is depicted as the flat second end 420 in FIG. 37, may be flat, nearly flat, rounded or sharp. In specific embodiments, the widths of the end of each of the opposed teeth (e.g., the flat second end 420 as depicted in FIG. 37) may be about 10 mm, about 9 mm, about 8 mm, about 7 mm, about 6 mm, about 5 mm, about 4 mm, about 3 mm, about 2 mm, about 1 mm about 0.9 mm, about 0.8 mm, about 0.7 mm, about 0.6 mm, about 0.5 mm, about 0.4 mm, about 0.3 mm, about 0.2 mm, or about 0.1 mm.

Figure 40:
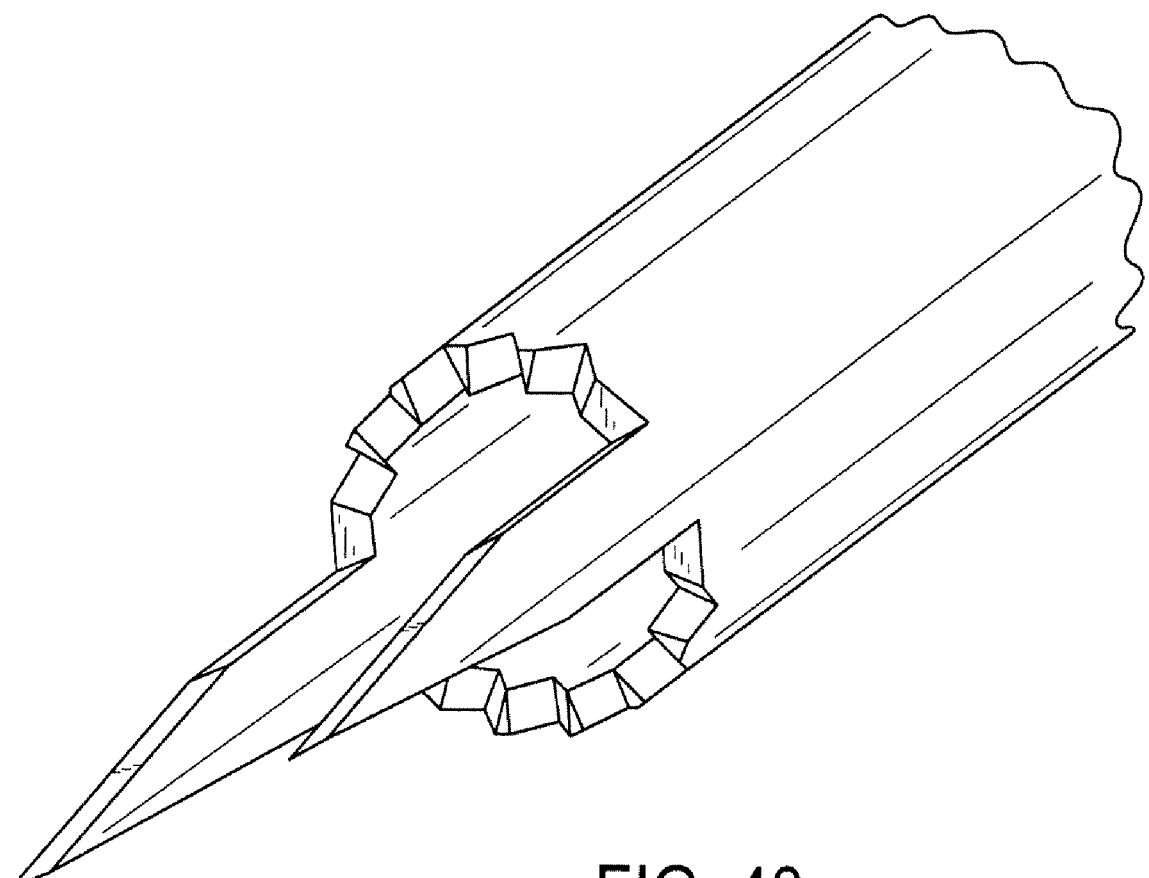
Figure 41:
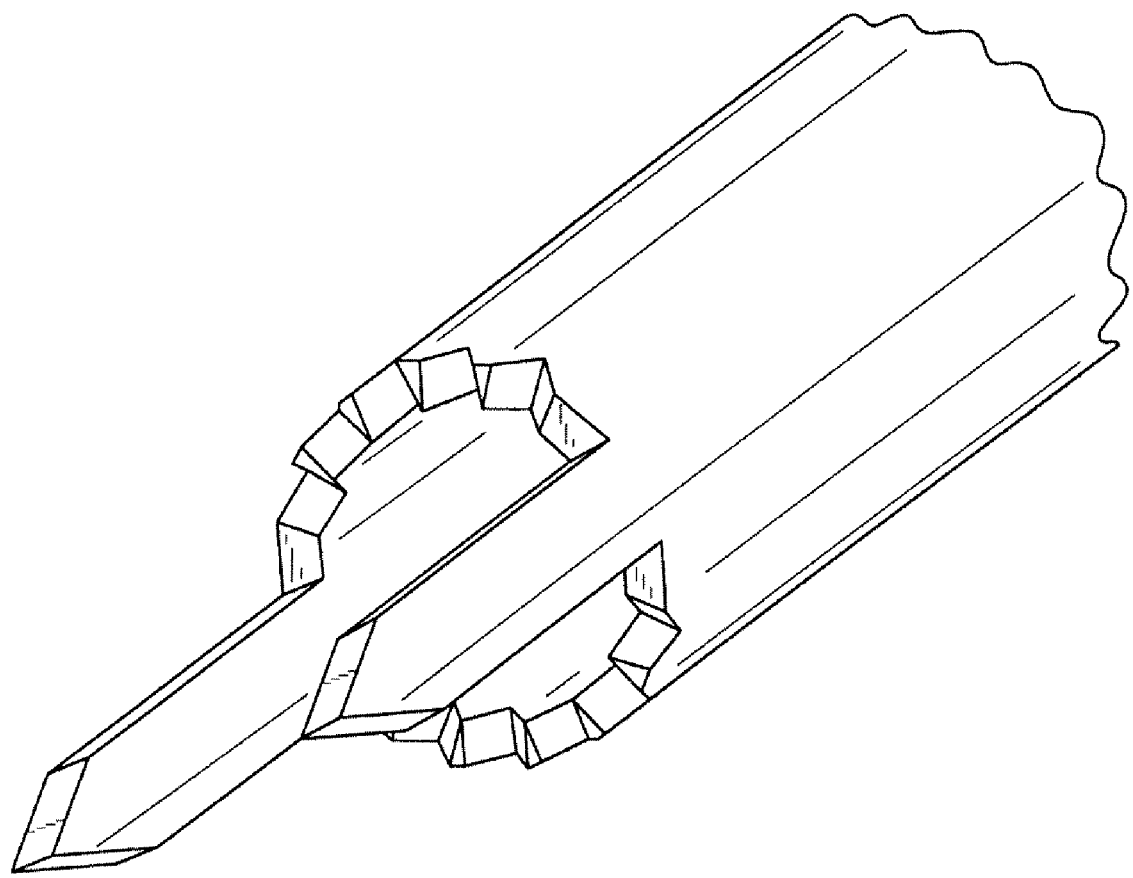
Figure 42:
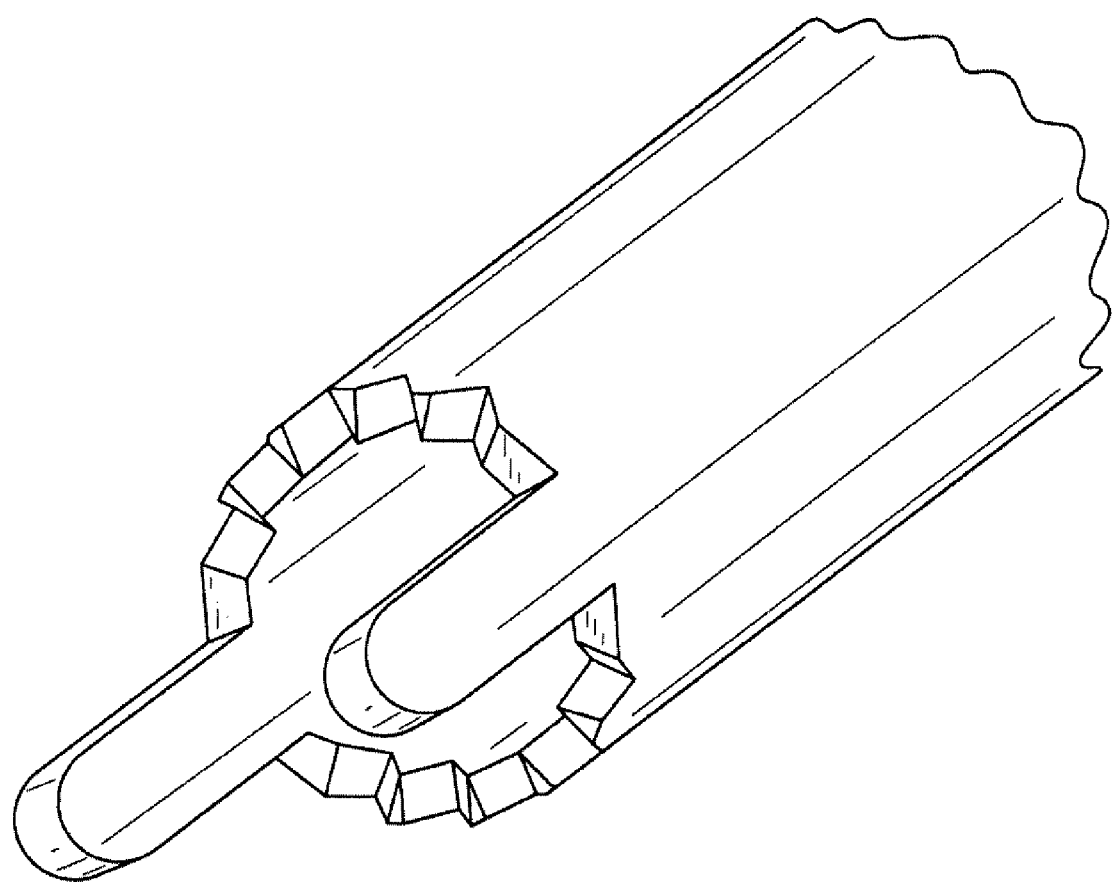
Figure 43:
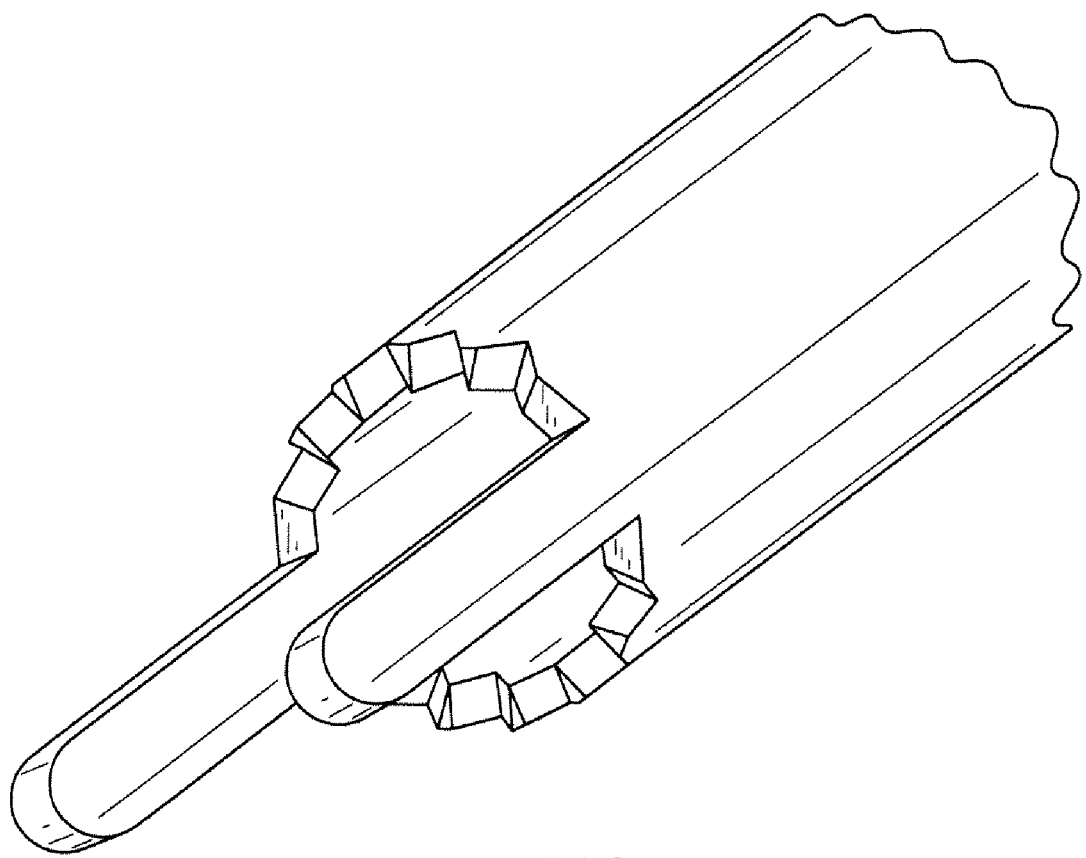

In another embodiment, the widths of the ends of the opposed teeth may have a contour as opposed to being flat. In another embodiment, the ends of the opposed teeth, and as depicted in FIGS. 39-41, may be pointed or sharp. In another embodiment, and as depicted in FIGS. 42-43, the ends of the opposed teeth may be rounded. Two opposed teeth are shown in FIGS. 37-43 for illustration, In various embodiments, there may be any number of teeth. Similarly, although specific portions (i.e., straight portion 407, tapered portion 410, angled portion 415, second flat end 420, and length 405 of the tapered portion 410 and the angled portion 415) are depicted in FIG. 37, both opposed teeth 50 may share similar portions as well as dimensions of the similar portions. In other embodiments, however, the portions or dimensions of the portions may be different between one of the opposed teeth and the other of the opposed teeth.

Figure 44:
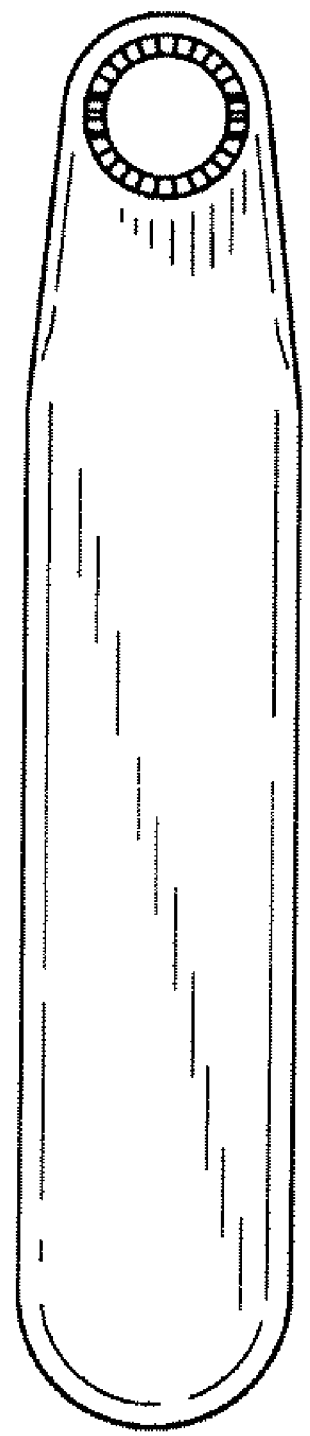
FIG. 44 shows an alternative view of the handle of the drill guide as depicted in FIGS. 35-36.
Figure 45:
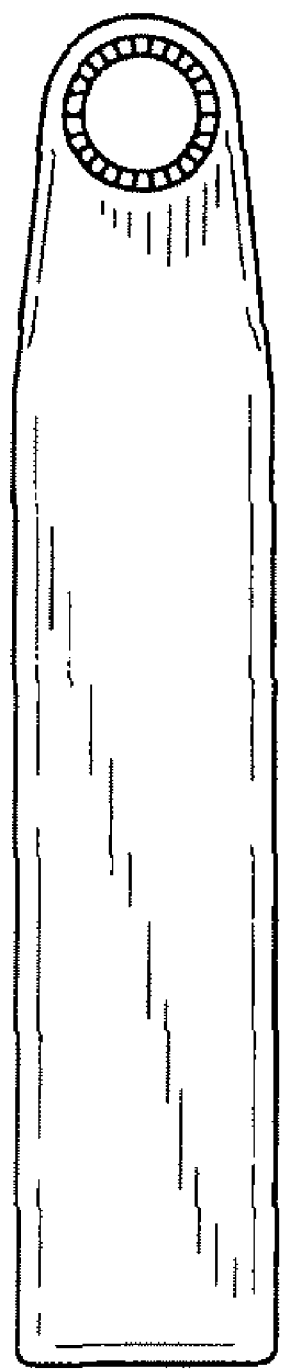
Figure 46:
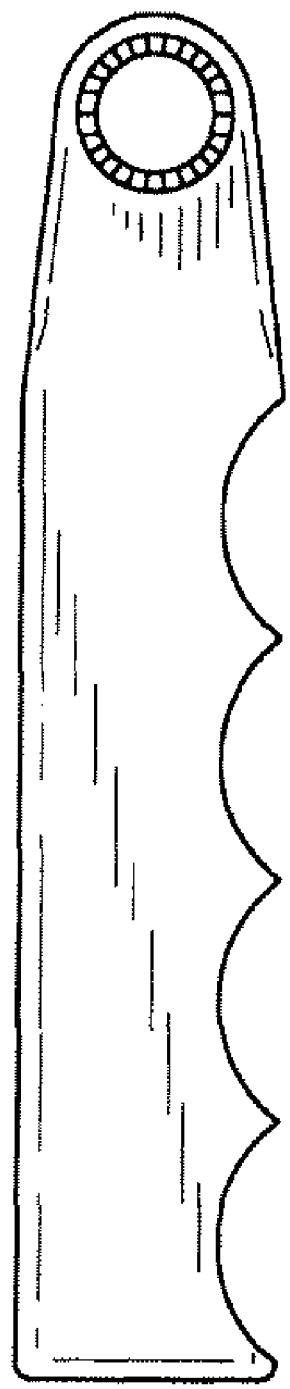
Figure 47:
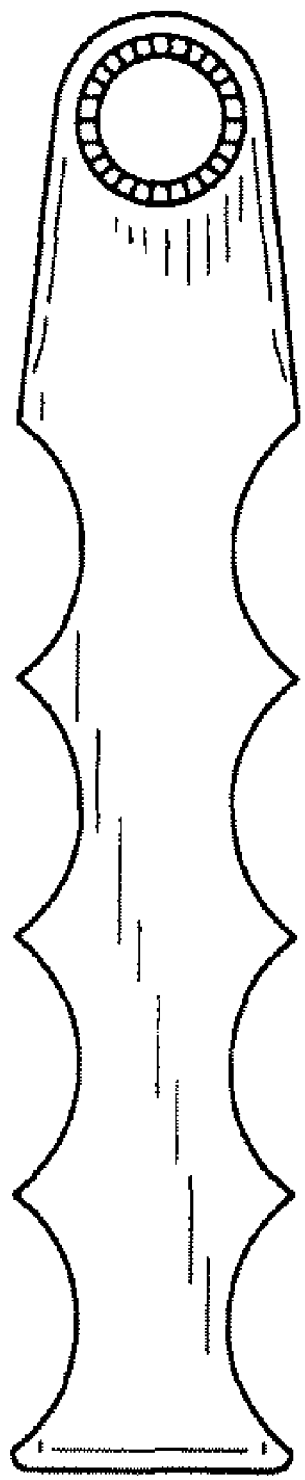
Figure 48:
Figure 49:
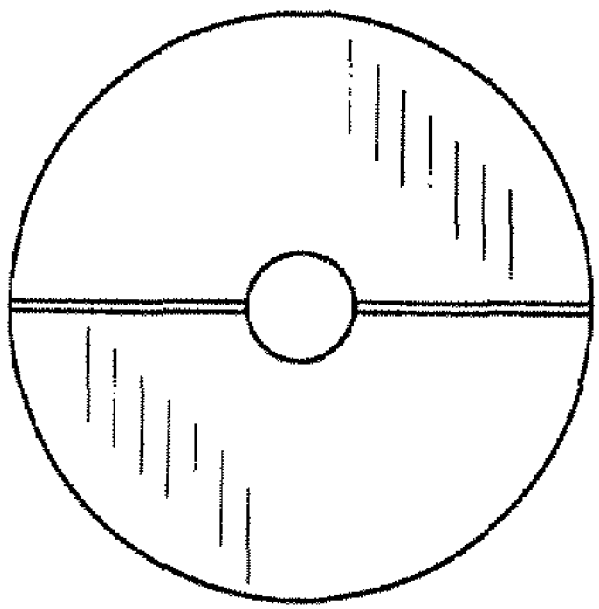
Figure 50:
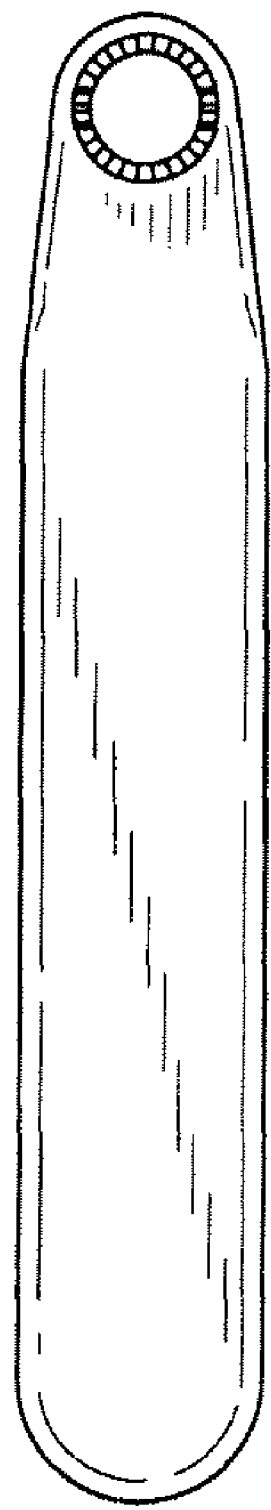

The handle on the drill guide may be configured in any suitable shape and size. In some embodiments, the handle on the drill guide is configured to permit the surgeon to manipulate the drill guide. In the embodiment depicted in FIG. 44, the handle is elongated with a rounded end. In alternative embodiments, the handle may have the shapes as depicted in FIGS. 45-50. In a the embodiment depicted in FIG. 45, the drill guide handle is elongated in a manner similar to that depicted in FIG. 44, but has an end that is substantially flat at the bottom. As depicted in FIG. 46, the handle may be scalloped on one side. In some such embodiments, the scalloping is configured to easily interact with the fingers of the surgeon as he grasps and manipulates the drill guide. In some such embodiments, the scalloping may enhance the surgeon's ability to manipulate the drill guide. As depicted in FIG. 47, the handle may be scalloped on two sides. In some such embodiments, the scalloping may enhance the surgeon's ability to manipulate the drill guide. In some embodiments, the proximate end of the drill guide comprises a knob. As depicted in a top plain view in FIG. 49 and a side view as in FIG. 48, the knob may be rounded. In another embodiment, the knob may be circular. In another embodiment, the handle may be tapered. In another embodiment, the handle may be various lengths. As depicted in FIG. 50, the handle may be longer as compared to FIGS. 44-47.

Figure 2:
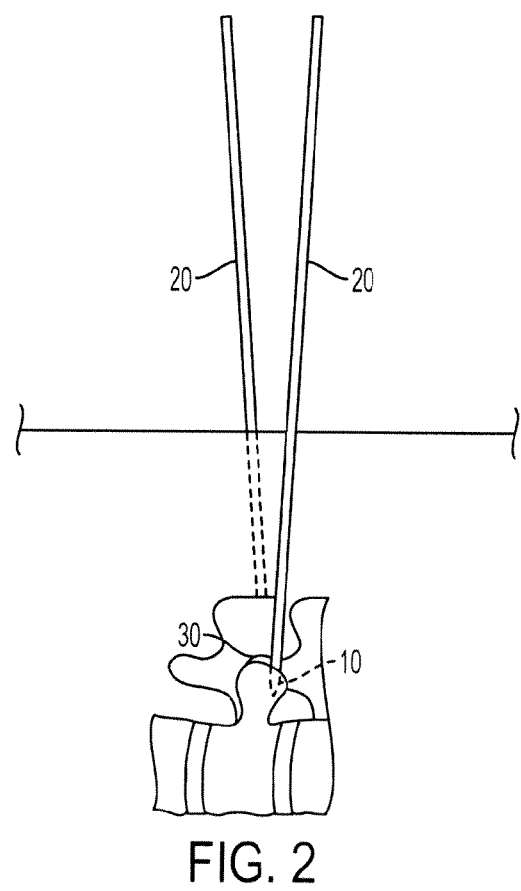
FIG. 2 shows an alternative view of facet joint location with surgical pins.

Turning to methods of the present invention, FIG. 1 represents a first step in an embodiment of the procedures of the present invention. In this step, following the creation of a small incision, the distal tips 10 of surgical pins 20 are used to locate facet joints 30. FIG. 2 depicts an alternative view of FIG. 1 showing the location of facet joints 30 with distal ends 10 of pins 20.

Figure 3:
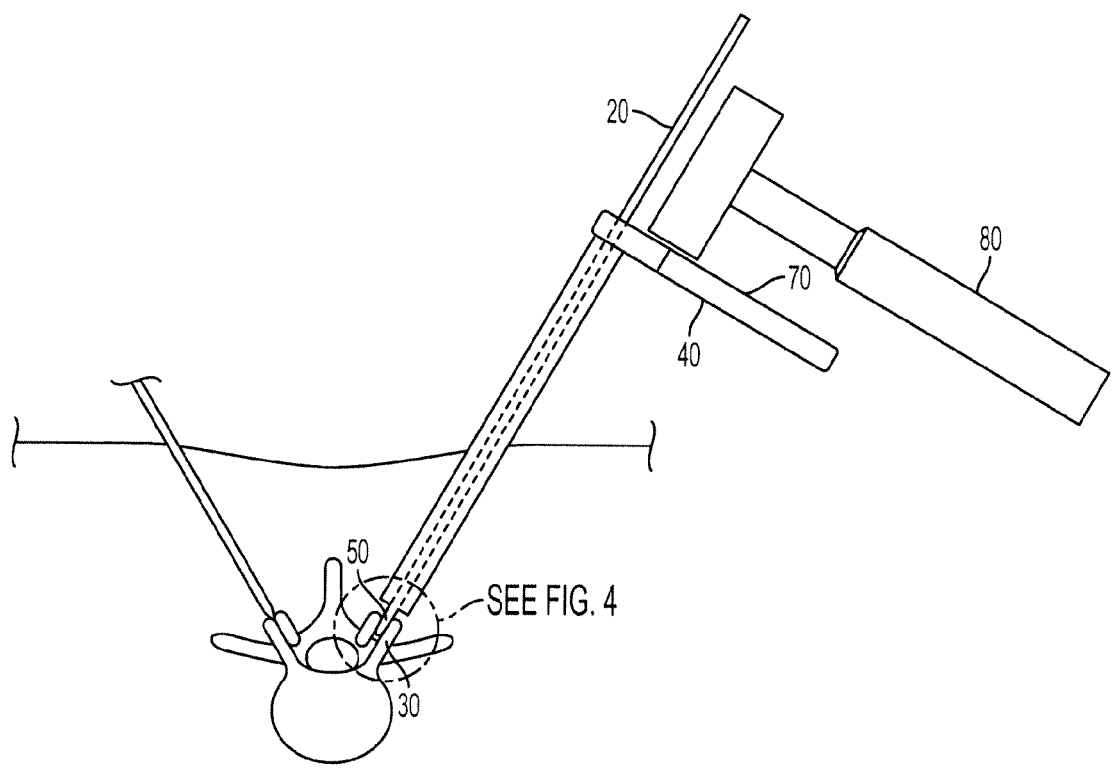
FIGS. 3-5 depict insertion of a drill guide directly over a surgical pin without the use of a spatula.

Once the facet joint 30 has been located with the distal end of a pin 20, as seen in FIG. 3, a substantially hollow drill guide 40 can be slid over the pin 20. The drill guide 40 can reach the facet joint 30 through progressive dilation of the intervening soft tissue (note, however, that the instrument design does not preclude its use in a classic open surgery or by access to the facet joint through an otherwise limited incision).

Figure 4:
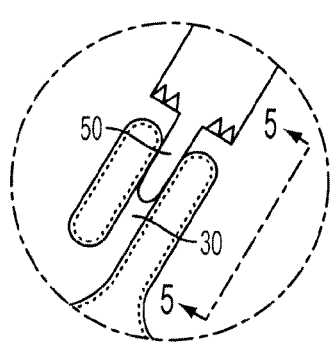
Figure 5:
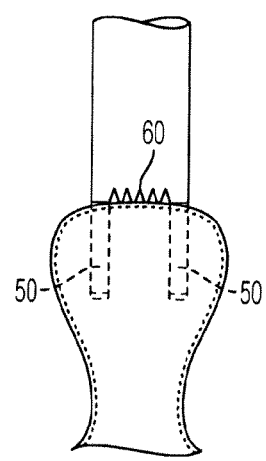

FIG. 4 depicts an enlarged view of the distal end of the drill guide within a facet joint 30. The distal end of the drill guide 40 can have one or more teeth 50. In certain embodiments, the distal end of the drill guide 40 has two or more opposed teeth 50 (FIG. 5) that are separated by about 180 degrees around the circumference of the distal end of the drill guide 40. In certain embodiments, the drill guide 40 can have a marking that indicates the rotational orientation of these opposed teeth 50. One or more smaller teeth 60 may also be found between or surrounding the opposed teeth 50. In general, the opposed teeth 50 may be inserted into the facet joint 30 as shown in FIGS. 3, 4 and 5. To achieve this insertion, the distal end of the drill guide 40 may simply be inserted into the facet joint 30. Alternatively or in combination, the handle 70 of the drill guide 40 may be tapped or hammered with a surgical hammer 80 to achieve insertion of the distal end of the drill guide into the facet joint 30.

Figure 30:
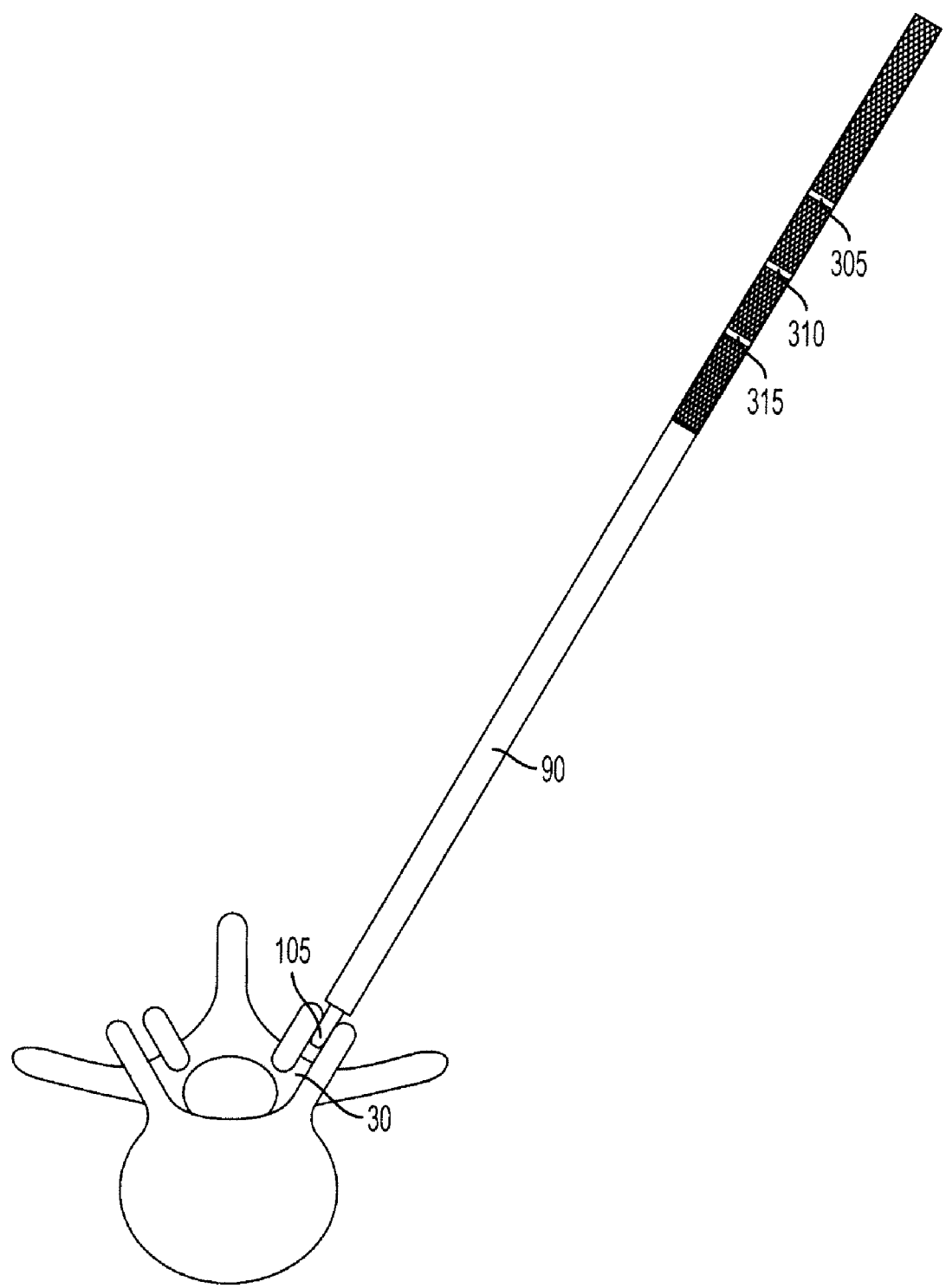
FIG. 30 shows an enlarged view of the spatula inserted in the facet joint without the insertion of the drill guide.
Figure 31:
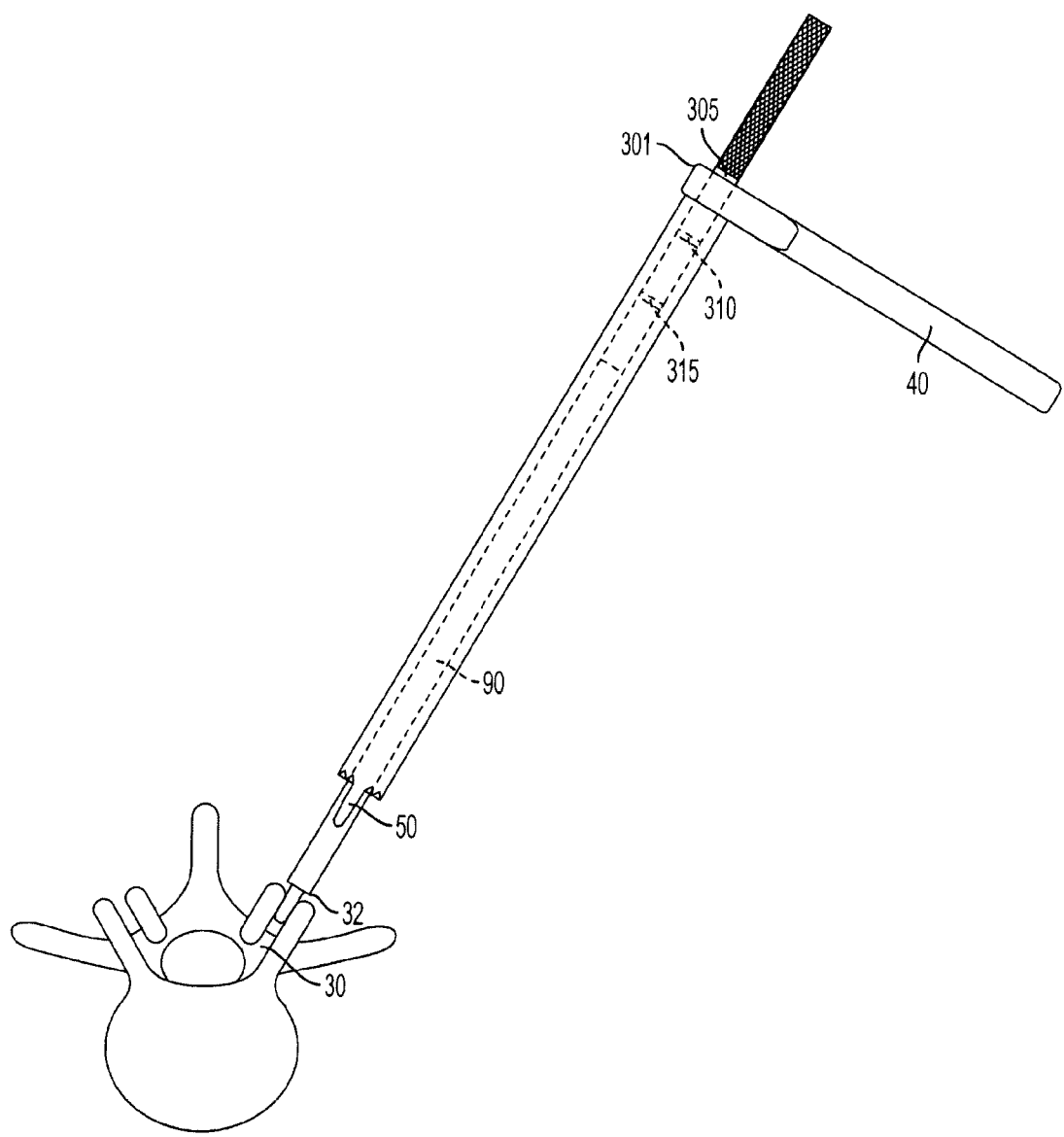
FIGS. 31-33 show the insertion of the drill guide at various positions over the spatula.

In a particular embodiment of the present invention, there can be an intermediate step between locating the facet joint 30 with the distal end 10 of a pin 20 and inserting the drill guide 40 over the pin 20. In this alternative embodiment, depicted in FIGS. 6-8, a substantially hollow spatula 90 is inserted over the pin 20. As depicted in FIG. 30, the distal end of the spatula 90 may comprise a planar wedge 105 that can be inserted into the facet joint 30. Further, as depicted in FIG. 31, the drill guide 40 may then be placed over the spatula 90 and inserted in the incision and advanced toward the facet joint 30.

A specific embodiment of the technique is depicted in FIGS. 30-33. In a specific embodiment of the technique, a spatula with transverse guide marks 300 may be used. In another embodiment, a spatula with one or more transverse guide marks 300 may be used. In one embodiment of the technique, a spatula with one transverse guide mark may be used.

In one specific embodiment of the technique, a drill guide 40 may be placed over the spatula 90 with one transverse guide mark and inserted in the incision towards the facet joint 30. The drill guide 40 may then be further inserted into the incision towards the facet joint 30 until the proximal end of the drill guide 301 aligns with the transverse guide mark on the spatula (for example, 305 on FIG. 31). Once this alignment occurs, the user can visually determine the alignment, which provides useful indicators to the user, surgeon or technician. In one embodiment, the alignment may indicate where the opposable teeth or distal end of the drill guide are located relative to various locations in the surgical technique, such as where the opposable teeth are in the body, relative to the facet joint.

The location of the transverse guide mark on the spatula can thus be located on various parts of the spatula. In one specific embodiment, the transverse guide mark is located on the spatula so when aligned with the proximal end of the drill guide 301, the opposable teeth of the drill guide are approaching the skin of the patient. In another specific embodiment, the transverse guide mark when aligned may indicate that the opposable teeth of the drill guide are approximately at the fascia of the patient. In another specific embodiment, the transverse guide mark when aligned may indicate that the opposable teeth are approximately at the muscle of the patient. In another specific embodiment, the transverse guide mark when aligned may indicate that the opposable teeth are approximately at the facet joint of the patient. In another specific embodiment, the transverse guide mark when aligned may indicate that the opposable teeth are approximately fully within of the patient. In another specific embodiment, the transverse guide mark when aligned may indicate that the opposable teeth are approximately about 10 mm within the facet joint of the patient.

In another specific embodiment, the alignment of the proximal end of the drill guide 301 with the transverse guide mark on the spatula may indicate to the user a change in behavior of the surgical technique is needed. In one specific embodiment, the transverse guide mark when aligned may indicate that the drill guide should be inserted more slowly or more carefully. In one specific embodiment, the transverse guide mark when aligned may indicate that the drill guide should only be rotated a few degrees in each direction.

Figure 10:
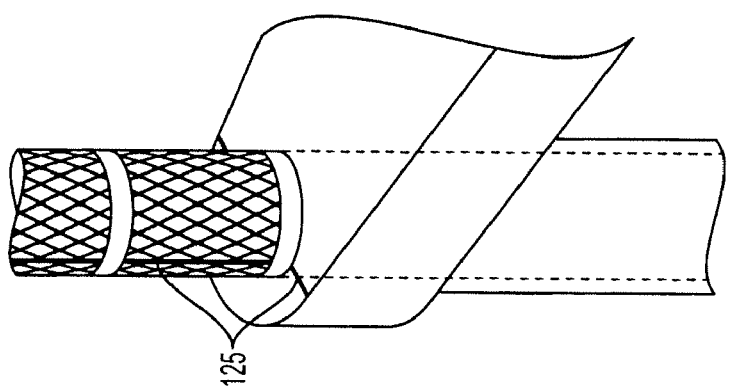
FIG. 10 depicts the alignment of markings on a spatula and drill guide to match the orientation of the distal ends of these tools.

In one embodiment, the transverse guide mark when aligned may indicate that the longitudinal marking on the spatula 115 and the markings on the handle of the drill guide can be aligned 125 so that the rotational orientation of the drill guide's two larger teeth 50 is in approximately the same plane defined by the spatula's planar wedge (FIGS. 9 and 10). In another embodiment, the transverse guide mark when aligned may indicate where the opposable teeth of the drill guide are located relative to the wedge of the spatula and/or the entrance into the facet joint. In one specific embodiment, the transverse guide mark when aligned may indicate that the opposable teeth of the drill guide are located about 10 mm from the proximate end of the wedge of the spatula. In another embodiment the distance may be from a range of about 1 mm to about 20 mm. In one embodiment, the transverse guide mark when aligned may indicate that the opposable teeth of the drill guide are located about 10 mm from the entrance of the facet joint. In another embodiment the distance may be from a range of about 1 mm to about 20 mm. In another embodiment, the transverse guide mark when aligned may indicate that the opposable teeth of the drill guide are at or approximately near the entrance of the facet joint.

Figure 32:
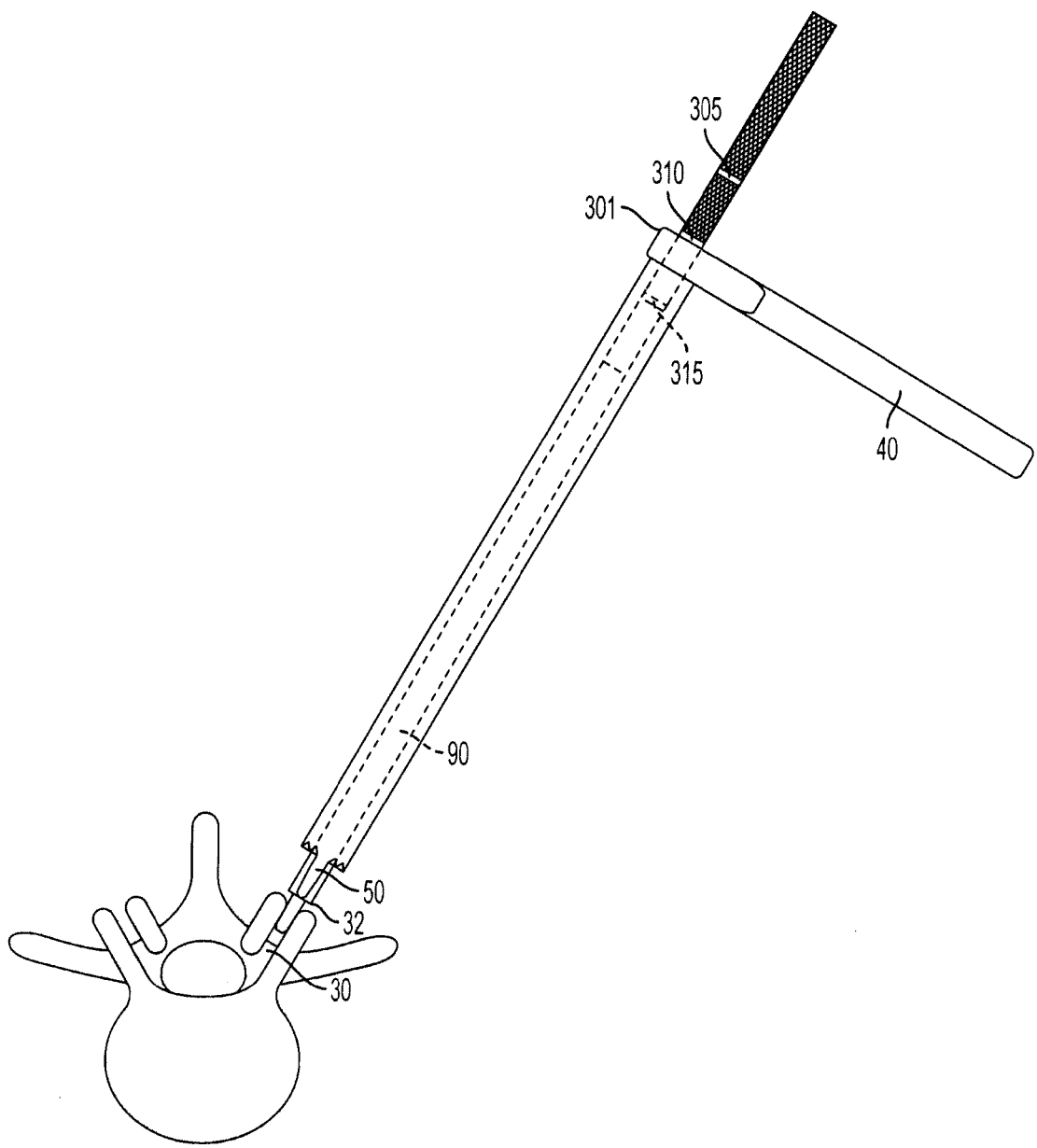
Figure 33:
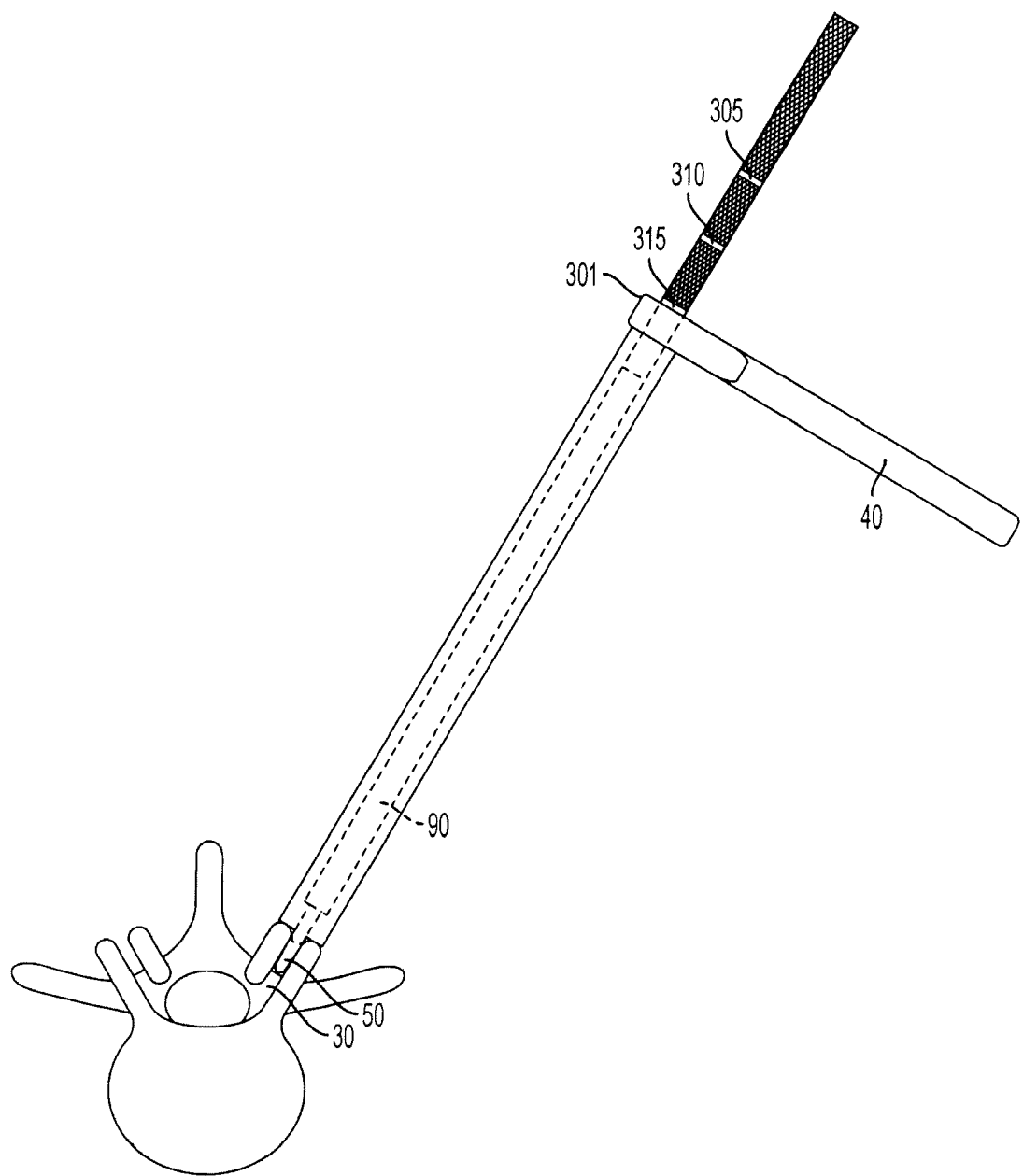

In one embodiment, the spatula may have multiple transverse guide marks. Thus, in one specific embodiment, multiple transverse guide marks may be placed on the spatula and thus provide multiple indicators to the user, surgeon or technician throughout the technique. In one embodiment, each transverse guide mark may be equidistant from each other. In one embodiment, each transverse guide mark may be from a range of about 1 mm to about 20 mm apart. In another embodiment, each transverse guide mark may be about 10 mm apart. In a specific embodiment of the technique, the spatula may have three, four or five transverse guide marks A specific embodiment of the technique may utilize the spatula with three transverse guide marks as depicted in FIG. 34 and the drill guide as depicted in FIG. 36. As depicted in FIG. 30, the distal end of the spatula 90 can have a planar wedge 105 that can be inserted into the facet joint 30. Further, as depicted in FIG. 31, the drill guide 40 may then be placed over the spatula 90 and inserted in the incision towards the body and inside the skin envelope. Once, inside the skin envelope, the drill guide 40 may then be further inserted in the incision. In a specific technique, the drill guide 40 may be rotated 360 degrees in a clockwise and then counterclockwise direction until it is past the fascial depth. Once past the fascia, the proximal end of the drill guide 301 will align with the first transverse guide mark on the spatula 305 as depicted in FIG. 31. At this point, and as depicted in FIGS. 9 and 10, the longitudinal marking on the spatula 115 and the markings on the handle of the drill guide can be aligned 125 so that the rotational orientation of the drill guide's two larger teeth 50 is in approximately the same plane defined by the spatula's planar wedge (FIGS. 9 and 10). The drill guide 40 may then be further inserted into the incision towards the facet joint 30. In a specific technique, the drill guide 40 may be gently rotated about 5 or 10 degrees in each direction to gently pass the drill guide 40 into and through the muscle. Regardless of the technique, the drill guide may be further inserted towards the facet joint 30 until the proximal end of the drill guide 301 aligns with the second transverse guide mark 310. This alignment is depicted in FIG. 32. This alignment indicates that the distal end of the drill guide meets up with the proximal end of the planar wedge of the spatula 32. Further, because the proximal end of the planar wedge of the spatula 32 is approximately at the level of the bone of the facet joint 30, this alignment also indicates that the distal end of the drill guide is at the entry level of the facet joint 30 or closely approaching it. At this point, the two large teeth of the drill guide may be aligned so that the rotational orientation of the drill guide's two larger teeth 50 is in approximately the same plane defined by the spatula's planar wedge (FIGS. 9 and 10) in order for the drill guide's two large opposed teeth 50 to be in the proper orientation to enter the facet joint 30. Once aligned in this manner, the two large teeth 50 can simply be inserted into the facet joint 30. A full insertion of the two large teeth 50 into the facet joint is indicated when the third transverse guide mark 315 aligns with the proximal end of the drill guide. In a specific embodiment, having the opposed teeth with a length of about 10 mm and a maximum width of about 3 mm therefore allows for a more stable and accurate procedure to be performed, including a more accurate and stable drilling into the facet joint and insertion, placement and fixation of the bone plug into the facet joint 30. The 3 mm length in width of the opposable teeth also aides in the insertion of the bone plug. The 3 mm width of the straight portion enters into the facet joint 30, therefore expanding the gap of the facet joint. This expansion therefore allows for easier insertion of the bone plug into the facet joint 30. Further, after the drill guide 40 is removed from the facet joint after implanting the drill guide, the facet joint may contract and allow the bone plug to sit more secured in the facet joint. This alignment is depicted in FIG. 33.

Alternatively, or in combination, and as shown in FIG. 9, a surgical hammer 80 or other appropriate tool may be used to tap or hammer the drill guide 40 to insert it into place within the facet joint 30. An alternate drill guide as depicted in FIG. 36 may be used. An alternate tip of the drill guide may be used as depicted in FIGS. 38-43. An alternate handle, as depicted in FIGS. 44-50 may be used.

Also, alternatively or in combination the above described methods can further comprise confirming the location of the pin, spatula and/or drill guide relative to the facet joint. In one embodiment, the confirming is accomplished with at least one x-ray. In a specific embodiment, a lateral x-ray is obtained.

Figures 11, 12:
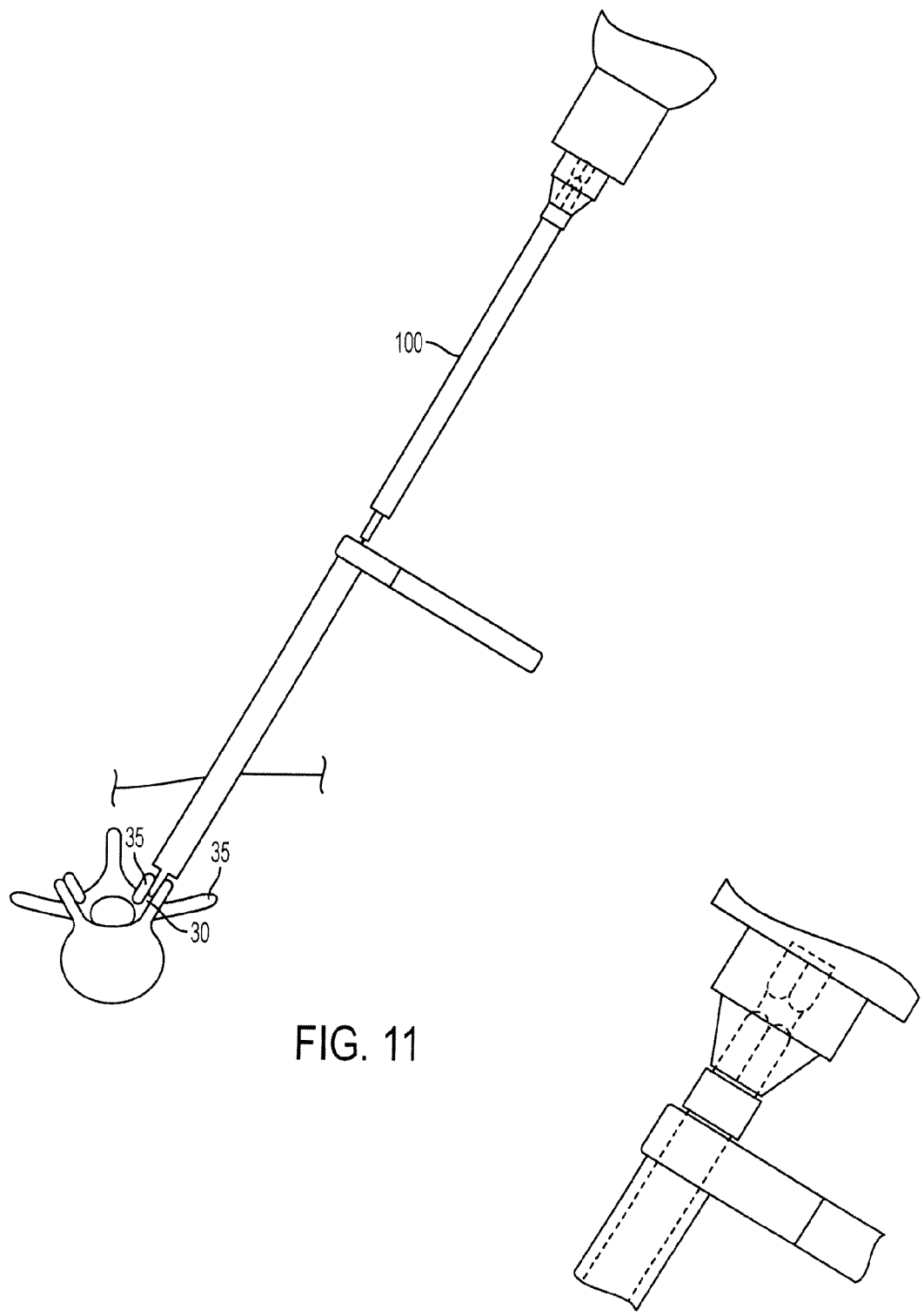
FIG. 11 shows the drill guide in position following removal of the surgical pin and/or spatula with a drill bit ready for insertion into the drill guide.
FIG. 12 shows an enlarged view of insertion of a drill bit into the drill guide.

Regardless of whether a spatula 90 is used following insertion of the distal end of the drill guide 40 into the facet joint 30, the pin 20 and/or spatula 90 can be removed from the substantially hollow inner portion of the drill guide 40. Following this removal, an appropriately-sized drill bit 100 is inserted through the substantially hollow portion of the drill guide 40. The drill bit 100 is used to create a hole between the bones 35 of facet joint 30 (see FIGS. 11 and 12). In some embodiments, the drill bit comprises a longitudinal axis and the drill guide comprises a longitudinal axis extending from the proximal end to the distal end. In these embodiments, the drill bit axis is concentric with the longitudinal axis of the drill guide. In some embodiments, the drill bit drills the hole in a manner that permits at least some of the drilled bone to remain in the hole. In some such embodiments, the drill grinds the drilled bone into a powder as it creates the hole. In some such embodiments, the drill bit compacts the drilled bone into the bone forming the hole. This compacted bone that remains in the drilled hole may help fusion of the facet joint by facilitating bone growth within the hole. The described drill bit (a punch could also be used) includes any number of components capable of performing the creation of a hole through both sides of the spinal facet joint.

As shown in FIG. 14, following the creation of a hole in the facet joint 30 a bone plug inserter 135 can be used to place a bone plug 145 into the hole. FIG. 13 shows an enlarged view of the distal end of a bone plug inserter 135 and its associated bone plug 145. As shown in FIG. 15, the bone plug 145 can simply be inserted into the facet joint 30, or, alternatively, or in combination, a surgical hammer 80 or other appropriate tool may be used to tap or hammer the bone plug inserter 135 to fix the bone plug 145 within the facet joint 30. Furthermore, any number of additional components capable of pushing and/or compressing a bone plug 145 into the hole can additionally be used. In certain particular embodiments, a suture or metallic overlay can also be applied to provide additional structural stability to the joint during bone plug 145 incorporation.

Figure 16:
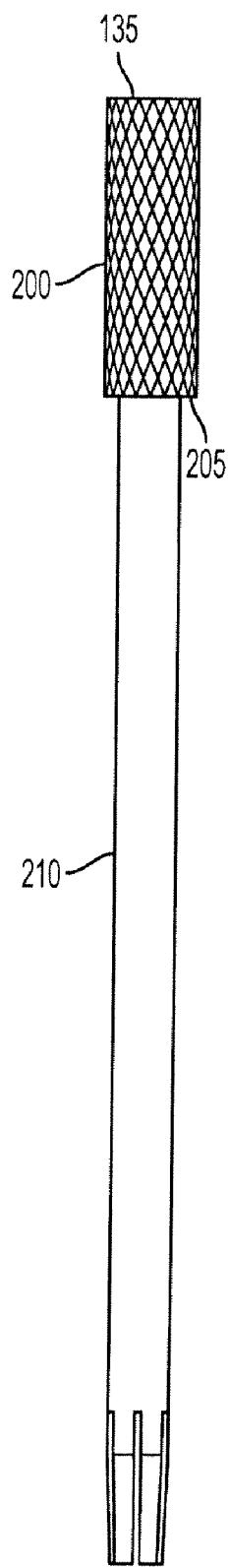
FIG. 16 shows a alternative design of a bone plug inserter that can be used in accordance with the present invention.

A specific embodiment of a bone plug inserter 135 is depicted in FIG. 16. In this embodiment, bone plug inserter 135 comprises a raised portion 200 at or near its proximal end. Raised portion 200 has dimensions that are greater than those of elongate portion 210. For example, in an embodiment where bone plug inserter 135 is substantially cylindrical, raised portion 200 may have a diameter greater than that of elongate portion 210. Raised portion 200 is configured to interact with the proximal portion of drill guide 40 in a manner that prevents passage of raised portion 200 into the substantially hollow portion of the drill guide 40. In a specific embodiment, the distal edge or surface of raised portion 200 at lip or ridge 205 contacts the proximal end of the drill guide 40. This configuration minimizes the chances of over-insertion of bone plug 110 into hole 28 and related damage. Over insertion in this context includes insertion of the bone plug 110 into hole to an extent that may cause damage to the bone plug 110, hole 28, or any portion of the facet joint. In some embodiments, over insertion occurs where the bone plug 110 is inserted to an extent that causes the distal end of the bone plug 110 to extend beyond the facet joint or proximal end of the bone plug 110 to be below the surface of the facet joint. Raised portion 200 may be any suitable size and configuration. For example, raised portion 200 may simply be a post or other structure that is configured to interact with the distal portion of drill guide 40.

Figure 17:
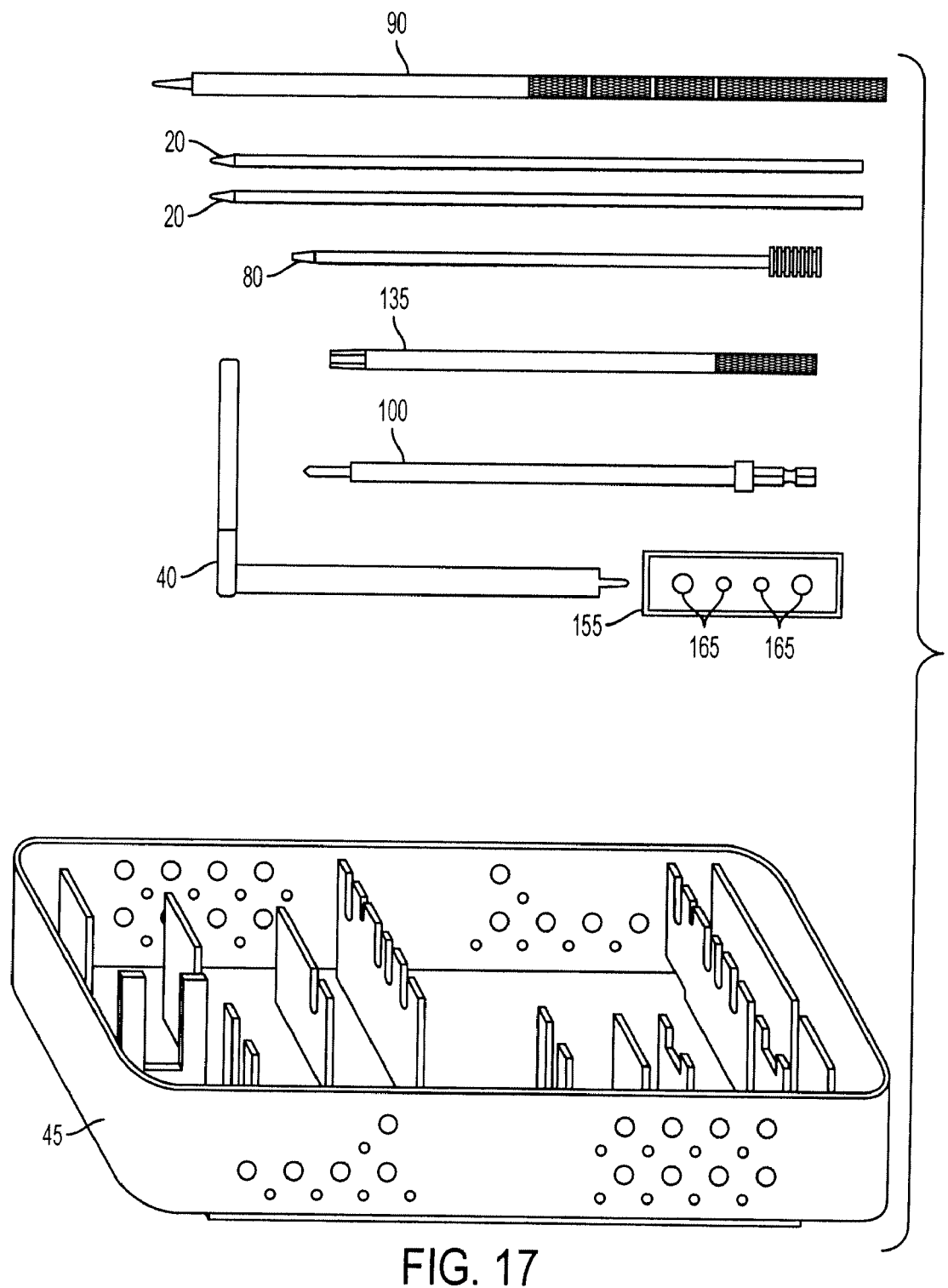
FIG. 17 shows surgical tools that can be used in accordance with the present invention in a combination that may be provided in a surgical kit.

FIG. 17 depicts tools that can be assembled into a surgical kit of the present invention. The depicted surgical kit includes pins 20, a spatula 90, a drill guide 40, a surgical hammer 80, a bone plug inserter 135, an appropriately-sized drill bit 100 and a bone plug holder 155. The depicted bone plug holder 155 has openings 165 shaped to hold variously sized or shaped bone plugs. Other surgical kits according to the present invention can include different combinations or subsets of these tools in varying numbers as deemed appropriate for particular needs and uses. Whatever combination of tools is chosen for a particular surgical kit according to the present invention, the tools are generally provided in an autoclavable container such as or similar to that depicted in FIG. 17. The tools may be configured such that they may be used in minimally invasive procedures (e.g., arthroscopic or percutaneous procedures).

Figure 18:
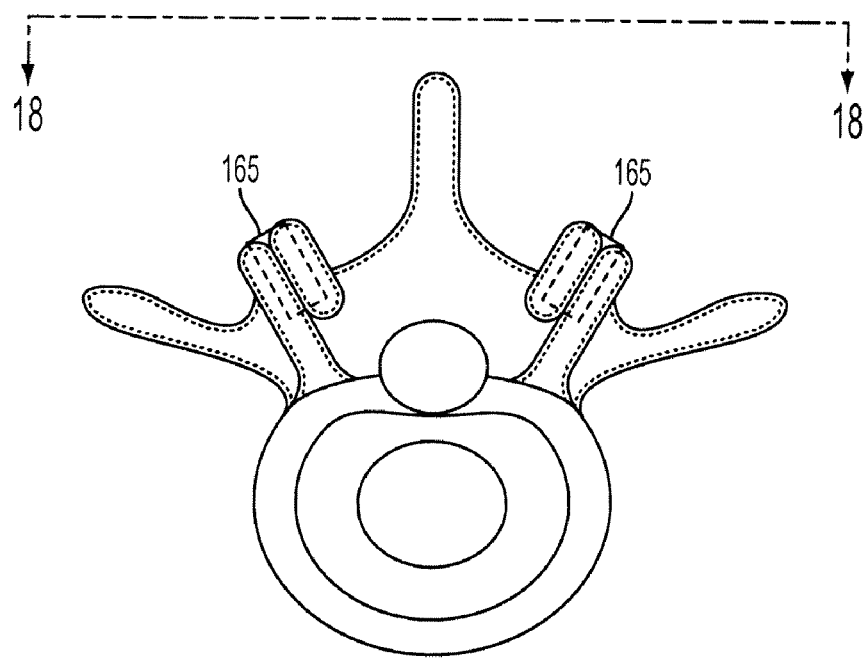
FIGS. 18 and 19 represent alternate views of holes created by drilling in the facet joints where bone plugs of the present invention can be inserted.
Figure 19:
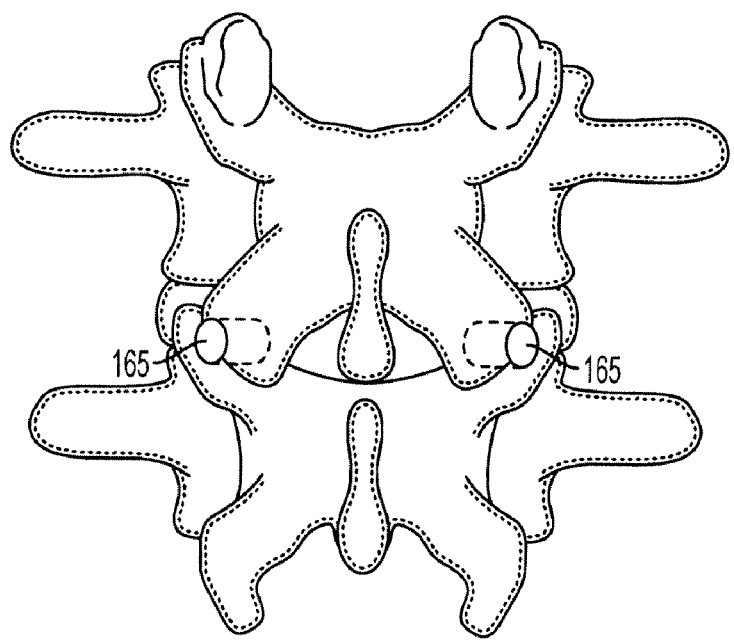

Holes 165 in facet joints created by the previously described drill bit are depicted in FIGS. 18 and 19. An alternative depiction of a hole 28 created by a drill bit in a facet joint between two facet joint bones 130 and 32 is provided in FIG. 20.

This FIG. 20 also shows one embodiment of a bone plug 110 according to the present invention. The bone plug 110 depicted in FIG. 20 is also shown in an enlarged alternative perspective in FIG. 21. This depicted bone plug 110 includes an inverted frustum shape. In certain embodiments according to the present invention, the distal end 22 of the bone plug 110 can be about 3 mm to about 8 mm in diameter and the proximal end 24 of the bone plug can be about 4 mm to about 12 mm in diameter. This general shape can be adopted to facilitate fixation during bone plug incorporation into the facet joint. The procedure is envisioned to require only one bone plug per facet joint and, if required, two bone plugs per facet joint level. Permanent fixation of the bone plugs should occur when bone in-growth occurs into the joint itself and into the plug over time.

Figure 23:
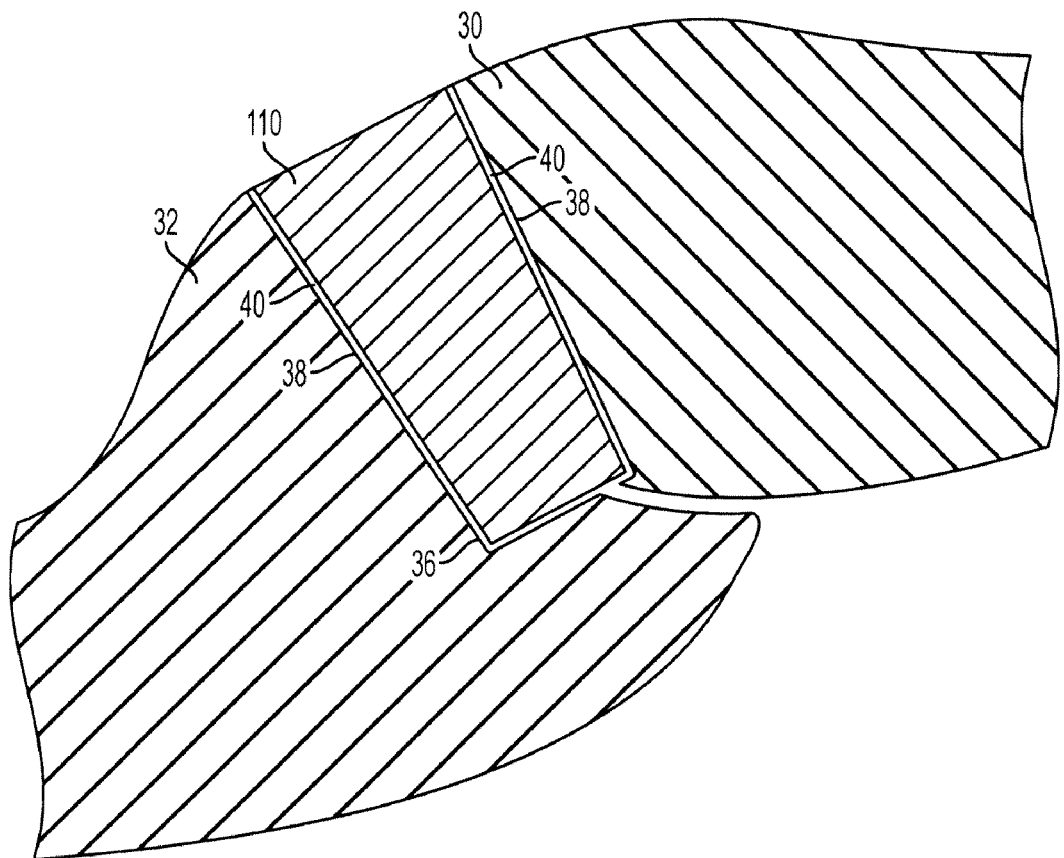
FIG. 23 is a cross-section depiction of FIG. 22.
Figure 24:
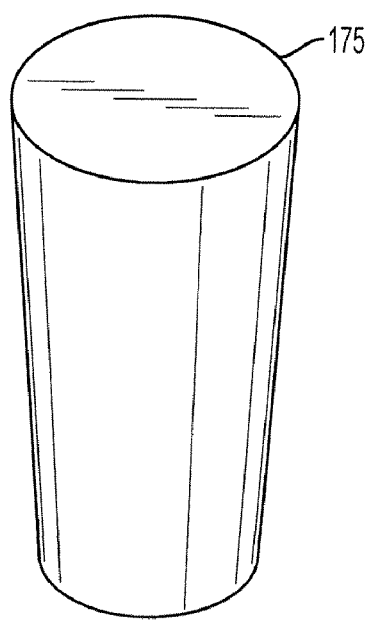
FIG. 24 shows a second alternative frustum shaped bone plug.
Figure 25:
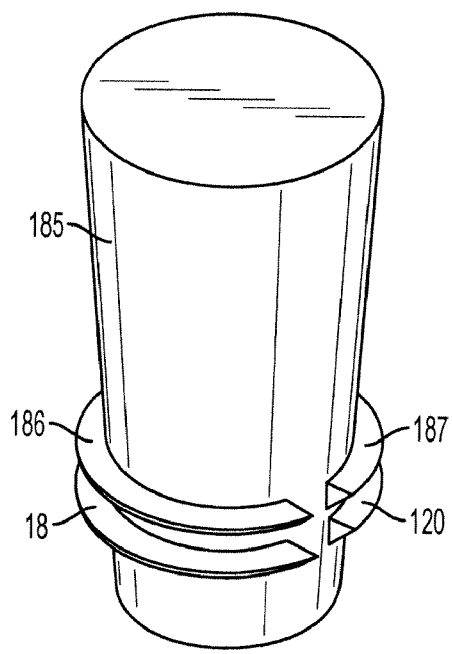
FIGS. 25-29 show a variety of bone plugs in with different configurations of fins, flanges and/or ridges.
Figure 26:
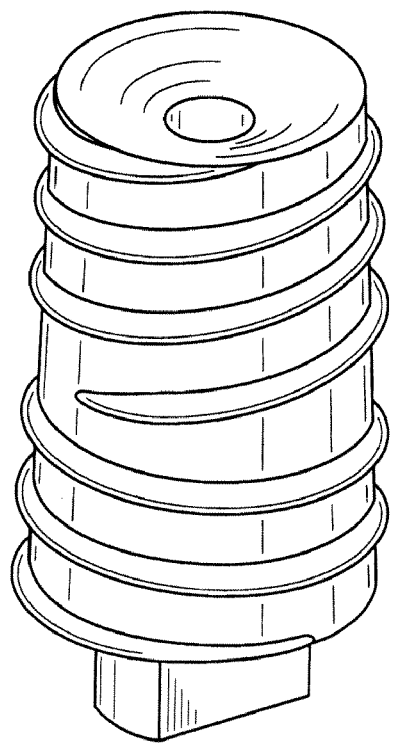
Figure 27:
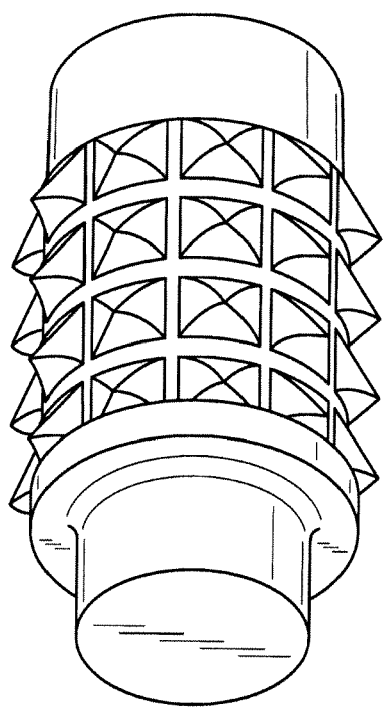
Figure 28:
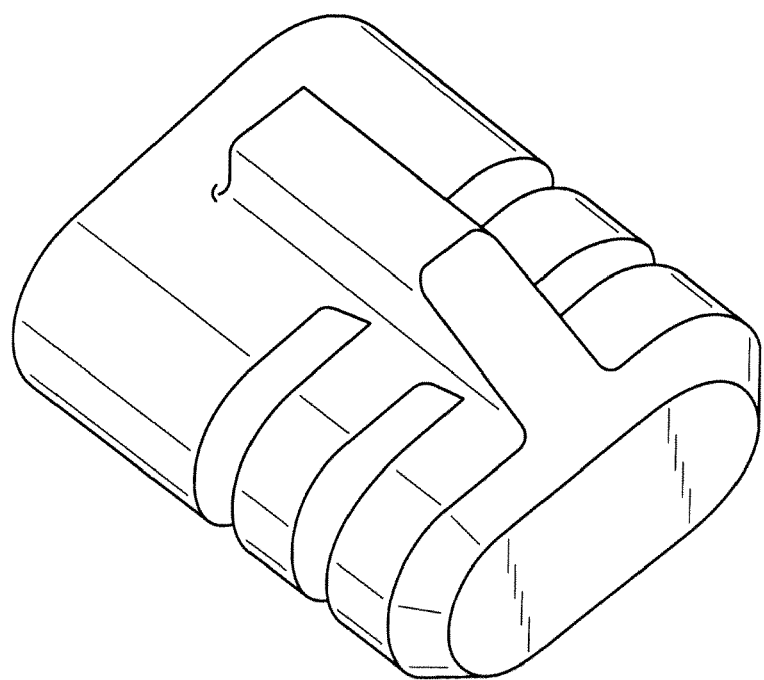
Figure 29:
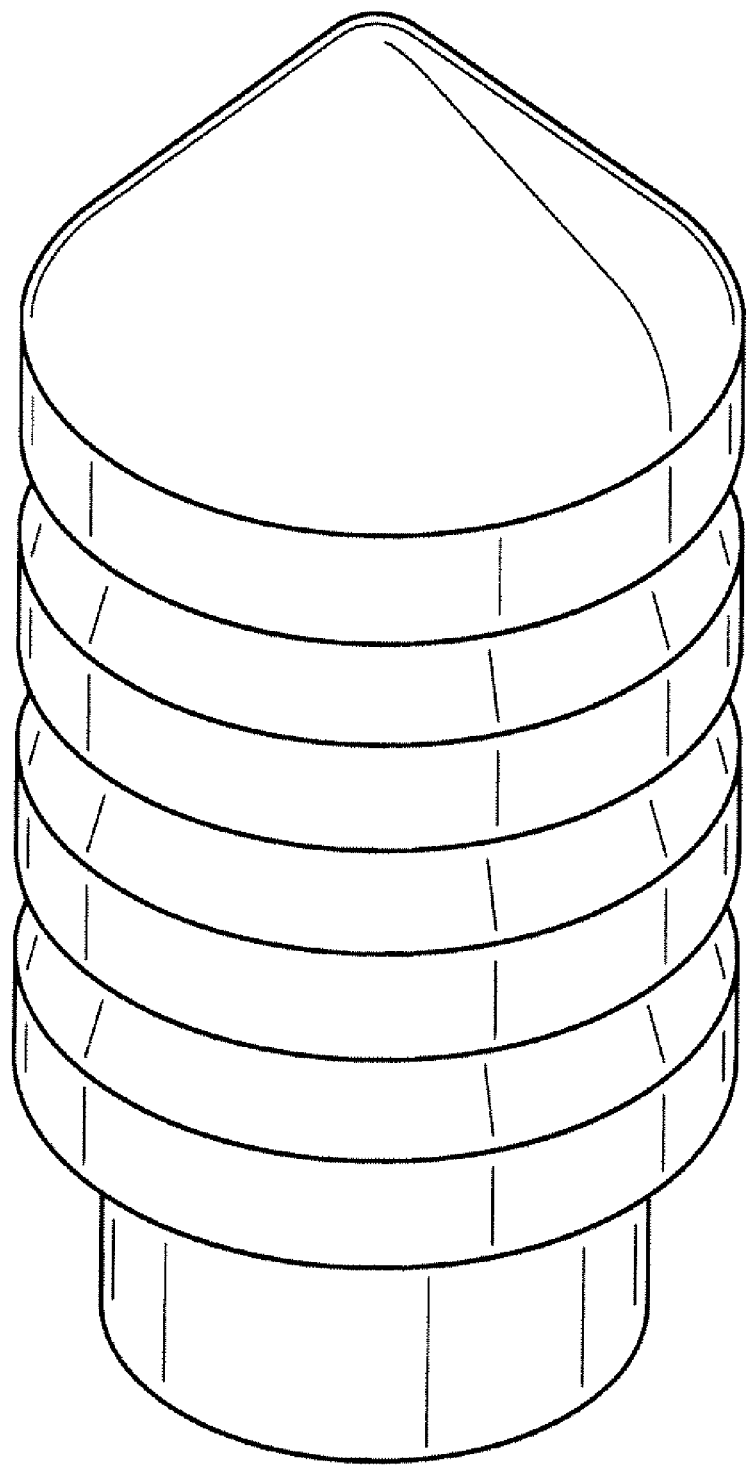

FIG. 22 shows a bone plug 110 inserted into a facet joint between facet joint bones 130, 32. FIG. 23 depicts a cross section of this bone plug within the facet joint. FIG. 24 shows an alternative bone plug 175 of the present invention. FIG. 25 shows another alternative bone plug 185 according to the present invention. This embodiment includes four fins or flanges 18, 120, 186, 187. FIGS. 26-29 show a variety of other bone plug designs for use in accordance with the present invention. Each design includes a different non-limiting example of a configuration of shapes be used and incorporated into the bone plugs used with the present invention. For example, the cross section of the distal and proximal ends of the bone plug may be the shape of a square, a rectangle, a triangle, a circle, a trapezoid, a pentagon, an octagon or an oval.

As should be understood by one of ordinary skill in the art, a bone plug of any appropriate shape, size can be used in accordance with the present invention.

Bone plugs according to the present invention can be formed of any suitable material. It should be understood that while the plugs according to the present invention are consistently referred to as "bone" plugs, they need not be formed out of bone in all circumstances. The key feature of these bone plugs is that they are formed of a material allowing bone in-growth and fixation over time. In some embodiments, the bone plugs of the present invention can be formed at least in part of any of the following: synthetic cortical bone, a harvested compacted synthetic iliac crest graft, an autologous allograft, a cadaveric allograft, autografts, bone substitutes such as coral granules or hydroxyapatite crystals, a trabecular or porous metal, a metal graft, synthetic iliac crest graft, a xenograft, synthetic graft, cortico-cancellous graft, and bone morphogenic proteins. In some embodiments, the bone plugs may also include or comprise proteins that enhance or promote bone growth. In one embodiment, the hole created in a facet joint can be filled with the patient's own harvested and compacted bone plug using iliac crest autograft. In other embodiments, the hole created in a facet joint can be filled with a pre-made, pre-shaped cortical cadaveric allograft (the autograft or allograft formed by bone plug press or machining). In further embodiments, the hole created in a facet joint can be filled with a FDA approved pre-made, pre-shaped synthetic graft.

In some embodiments, the bone plugs may include biocompatible granules, which are a hard substance that provides structural support or physiological advantages to the implant mass. The biocompatible granules can be made of synthetic, naturally occurring, polymeric, or non-polymeric materials. In one embodiment, the granules are also biodegradable such that the implant degrades over time and may be replaced with native bone tissue. The biocompatible granules of the present invention can be made of a synthetic, biocompatible material, such as biopolymers, bioglasses, bioceramics, calcium sulfate, silicon oxide, calcium phosphate such as, for example, monocalcium phosphate monohydrate, monocalcium phosphate anhydrous, dicalcium phosphate dihydrate, dicalcium phosphate anhydrous, tetracalcium phosphate, calcium orthophosphate phosphate, calcium pyrophosphate, α-tricalcium phosphate, β-tricalcium phosphate (β-TCP), apatite such as hydroxyapatite (HA), or polymers such as, for example, poly(α-hydroxyesters), poly(ortho esters), poly (ether esters), polyanhydrides, poly(phosphazenes), poly (propylene fumarates), poly(ester amides), poly(ethylene fumates), poly(amino acids), polysaccharides, polypeptides, poly(hydroxy butyrates), poly(hydroxy valerates), polyurethanes, poly(malic acid), polylactides, polyglycolides, polycaprolactones, poly(glycolide-co-trimethylene carbonates), polydioxanones, or copolymers, terpolymers thereof or blends of those polymers, or a combination of biocompatible and biodegradable materials.

The following materials can also be used as a structural component in the bone plugs of the present invention and are considered to be synthetic materials: Chitin and chitosan, which may be derived form tissues of marine non-vertebrate animals; hyaluronic acid, a polysaccharide, which can be obtained from rooster comb or by microorganism fermentation; poly(amino acids) and polypeptides, which may be produced by biotechnological processes; any polysaccharide, which is obtained from plants, from non-vertebrate animals or by biotechnological processes (e.g. alginate).

Calcium phosphate ceramics are biocompatible and can be used in various biomedical applications. HA and β-TCP bioceramics are particularly useful materials because they have similar ionic properties as the mineral components of bone. In addition, their resorption kinetics can be controlled to meet the needs of a specific therapy. Furthermore, because β-TCP is biodegradable, it is absorbed in vivo and can be replaced with new bone growth.

Other equivalent elements can be substituted for the elements disclosed herein to produce substantially the same results in substantially the same way.

It is anticipated that the availability of the methods and surgical kits described herein will dramatically increase the number of surgeries performed because they can offer the first safe outpatient surgical solution to the predominant cause of spinal joint pain. It is expected that many patients receiving this procedure will be able to walk out the same day and be fully functional within a few weeks. Present surgical solutions require hospitalization of about three days and six to twenty-four months recovery.

Aside from the obvious positive clinical outcome, the significant favorable financial impact on disability, worker's compensation and health care insurers is considerable. First, the present invention provides a minimally invasive surgery that often can be performed in an outpatient setting as opposed to major surgery performed in a hospital. This procedure can also be performed during open surgery if the facet joints need to be fused as determined by a physician particularly in conjunction with instrumented vertebral fusion. Second, recovery times are estimated to be a few weeks as opposed to 6 to 12 months, and finally, the present invention is directed at overcoming, or at least improving upon, the disadvantages of the prior art by achieving the following: reduced morbidity; reduced blood loss; reduced time under anesthesia; reduced risk; reduced recovery time; reduced risk of post-operative infection; and minimal scarring that decreases the risk of failed back syndrome and improves revision surgery outcome. Furthermore, the present invention does not preclude other surgical or non-invasive treatment options.

While specific embodiments of the present invention have been described, other and further modifications and changes may be made without departing from the spirit of the invention. All further and other modifications and changes are included that come within the scope of the invention as set forth in the claims. The disclosures of all publications cited above are expressly incorporated by reference in their entireties to the same extent as if each were incorporated by reference individually.

What is claimed is:

1. A method comprising:
   creating an incision;
   locating a facet joint with a distal end of a pin wherein said facet joint is formed between two opposing facet joint bones and said pin comprises said distal end and a proximal end;
   sliding a substantially hollow spatula over said pin wherein said spatula comprises a proximal end, a distal end and a body wherein said distal end comprises a planar wedge, and said body comprises a longitudinal marking that can indicate the orientation of said planar wedge and one or more transverse guide markings near the proximal end of said spatula;
   adjusting the rotation of said planar wedge until said planar wedge enters said facet joint;
   sliding a substantially hollow drill guide over said spatula wherein said drill guide comprises a proximal end, a distal end, a longitudinal axis extending from the proximal end to the distal end and a handle wherein said handle is nearer to the proximal end of the drill guide than to the distal end, said distal end comprises two opposed teeth that can be inserted into said facet joint and a marking on said proximal end that can be aligned with said longitudinal marking on said spatula thereby allowing the orientation of said opposed teeth to be in approximately the same plane defined by said planar wedge;
   inserting said drill guide into said incision until said proximal end of the drill guide aligns with said first transverse guide mark on said spatula;
   aligning said longitudinal marking on said spatula with said marking on said drill guide thereby aligning said opposed teeth in approximately the same plane defined by said planar wedge;
   further inserting said drill guide into said incision and using said one or more transverse guide markings to indicate the depth of the insertion of said teeth of said drill guide into said facet joint;
   removing said spatula from within said drill guide;
   inserting a drill bit into said drill guide, wherein the drill bit comprises a longitudinal drill bit axis, and wherein the drill bit axis is concentric with the longitudinal axis;
   drilling a hole into said facet joint by simultaneously drilling the two opposing facet joint bones;
   removing said drill bit;
   inserting a facet joint bone plug into said hole using a bone plug inserter having a raised portion at or near its proximal end, wherein said raised portion prevents over-insertion of said bone plug; and
   removing said drill guide.

2. A method according to claim 1 wherein said spatula comprises between one transverse guide mark to five transverse guide marks.

3. A method according to claim 2 wherein said spatula comprises three transverse guide marks.

4. A method according to claim 3 wherein a first transverse guide mark is near the proximal end of said spatula, a second transverse guide mark that is further from the proximal end of said spatula than said first transverse guide mark, and a third transverse guide mark that is further from the proximal end of said spatula than said second transverse guide mark.

5. A method according to claim 4 wherein the step of inserting said drill guide into said incision further comprises inserting said drill guide into said incision until said proximal end of the drill guide aligns with said first transverse guide mark on said spatula;
   aligning said longitudinal marking on said spatula with said marking on said drill guide thereby aligning said opposed teeth in approximately the same plane defined by said planar wedge;
   further inserting said drill guide into said incision until said proximal end of the drill guide aligns with said second transverse guide mark on said spatula, thereby indicating that said distal end of said drill guide is at the entry level of said facet joint or closely approaching it;
   further aligning said longitudinal marking on said spatula with said marking on said drill guide thereby assuring said opposed teeth are in approximately the same plane defined by said planar wedge; and
   further inserting said drill guide into said incision until said proximal end of the drill guide aligns with said third transverse guide mark on said spatula, thereby indicating that said opposed teeth are fully inserted or approximately fully inserted into said facet joint.

6. A method according to claim 2 wherein said transverse guide marks are equidistant from each other.

7. A method according to claim 2 wherein said transverse guide marks are about 1 mm to about 20 mm apart from each other.

8. A method according to claim 7 wherein said transverse guide marks are about 10 mm apart from each other.

9. A method comprising:

creating an incision;

locating a facet joint with a distal end of a pin wherein said facet joint is formed between two opposing facet joint bones and said pin comprises said distal end and a proximal end;

sliding a substantially hollow spatula over said pin wherein said spatula comprises a proximal end, a distal end and a body wherein said distal end comprises a planar wedge, and said body comprises a longitudinal marking that can indicate the orientation of said planar wedge, and one or more transverse guide markings near the proximal end of said spatula;

adjusting the rotation of said planar wedge until said planar wedge enters said facet joint;

sliding a substantially hollow drill guide over said spatula wherein said drill guide comprises a proximal end, a distal end wherein said distal end comprises opposed teeth with a length longer than about 3 mm that can be inserted into said facet joint, a longitudinal axis extending from the proximal end to the distal end, a handle wherein said handle is nearer to the proximal end of the drill guide than to the distal end, and a marking on said proximal end that can be aligned with said longitudinal marking on said spatula thereby allowing the orientation of said opposed teeth to be in approximately the same plane defined by said planar wedge, and;

inserting said drill guide into said incision until said proximal end of the drill guide aligns with said first transverse guide mark on said spatula;

aligning said longitudinal marking on said spatula with said marking on said drill guide thereby aligning said opposed teeth in approximately the same plane defined by said planar wedge;

further inserting said drill guide into said incision until said proximal end of the drill guide aligns with said second transverse guide mark on said spatula, thereby indicating that said distal end of said drill guide is at the entry level of said facet joint or closely approaching it;

further aligning said longitudinal marking on said spatula with said marking on said drill guide thereby assuring said opposed teeth are in approximately the same plane defined by said planar wedge;

further inserting said drill guide into said incision and using said one or more transverse guide markings to indicate the depth of the insertion of said teeth of said drill guide into said facet joint;

removing said spatula from within said drill guide;

inserting a drill bit into said drill guide, wherein the drill bit comprises a longitudinal drill bit axis, wherein the drill bit axis is concentric to the longitudinal axis;

drilling a hole into said facet joint by simultaneously drilling the two opposing facet joint bones;

removing said drill bit;

inserting a facet joint bone plug into said hole using a bone plug inserter having a raised portion at or near its proximal end, wherein said raised portion prevents over-insertion of said bone plug;

removing said drill guide; and closing said incision wherein said pin has also been removed prior to said closing of said incision.

10. A method according to claim 9 wherein said opposed teeth are a length of about 10 mm.

11. A method according to claim 9 wherein said opposed teeth comprise a straight portion and a tapered portion wherein said straight portion is about 3 mm in length and at the proximal end of said teeth, and said tapered portion is about 7 mm in length and at the distal end of said teeth.

12. A method according to claim 9, wherein one of said opposed teeth comprises a straight portion with a first end and a second end, a tapered portion with a first end and a second end, said first end of said tapered portion being disposed at said second end of said straight portion, and an angled portion with a first end and a flat second end, said first end of said angled portion being disposed at said second end of said tapered portion, wherein said straight portion is about 3 mm in length and about 3 mm in width, said tapered portion and said angled portion, together, is about 7 mm in length, said tapered portion comprises a slight taper from said first end of said tapered portion to said second end of said tapered portion until said tapered portion is about 2.25 mm in width, said angled portion comprises a second taper at an angle of about 45 degrees, thereby providing a more extreme narrowing at said flat end of said angled portion.

13. A method according to claim 9 wherein said spatula comprises three transverse guide marks.

14. A method according to claim 13 wherein said transverse guide marks are about 10 mm apart from each other.

15. A method according to claim 13 wherein a first transverse guide mark is near the proximal end of said spatula, a second transverse guide mark that is further from the proximal end of said spatula than said first transverse guide mark, and a third transverse guide mark that is further from the proximal end of said spatula than said second transverse guide mark.

16. A method according to claim 15 wherein the step of inserting said drill guide into said incision further comprises inserting said drill guide into said incision until said proximal end of the drill guide aligns with said first transverse guide mark on said spatula;

aligning said longitudinal marking on said spatula with said marking on said drill guide thereby aligning said opposed teeth in approximately the same plane defined by said planar wedge;

further inserting said drill guide into said incision until said proximal end of the drill guide aligns with said second transverse guide mark on said spatula, thereby indicating that said distal end of said drill guide is at the entry level of said facet joint or closely approaching it;

further aligning said longitudinal marking on said spatula with said marking on said drill guide thereby assuring said opposed teeth are in approximately the same plane defined by said planar wedge; and further inserting said drill guide into said incision until said proximal end of the drill guide aligns with said third transverse guide mark on said spatula, thereby indicating that said opposed teeth are fully inserted or approximately fully inserted into said facet joint.

17. A method according to claim 9 wherein said distal end of said drill guide comprises a plurality of teeth, wherein the plurality of teeth comprises two opposed teeth and one or more smaller teeth disposed between said two opposed teeth.

18. A method according to claim 9 wherein said inserting of said facet joint bone plug into said hole comprises sliding an inserter instrument into said drill guide wherein said inserter instrument has a proximal end and a distal end and a facet joint bone plug associated with said distal end; and disengaging the facet joint bone plug from said distal end of said inserter instrument into said drilled hole.

19. A method according to claim 9 further comprising tapping said spatula further into said facet joint following the initial inserting of said planar wedge into said facet joint.

20. A method according to claim 9 further comprising tapping said drill guide following said aligning of said markings so that said opposed teeth of said drill guide engage facet joint bone to secure the orientation of said drill guide until said removing of said drill guide.

21. A method according to claim 9 further comprising tapping said facet joint bone plug into said facet joint following said inserting.

* * * * *

UNITED STATES PATENT AND TRADEMARK OFFICE
CERTIFICATE OF CORRECTION

PATENT NO. : 7,837,713 B2
APPLICATION NO. : 12/404273
DATED : November 23, 2010
INVENTOR(S) : David A. Petersen It is certified that error appears in the above-identified patent and that said Letters Patent is hereby corrected as shown below:

Face of the Patent, Abstract, lines 11-12:
"using a bone plug inserter having a raised portion at or near is proximal end" should read -- using a bone plug inserter having a raised portion at or near its proximal end --.

Claim 1, column 24, lines 1-3:
"inserting said drill guide into said incision until said proximal end of the drill guide aligns with said first transverse guide mark on said spatula" should read -- inserting said drill guide into said incision until said proximal end of the drill guide aligns with a first transverse guide mark of said one or more transverse guide markings on said spatula --.

Claim 4, column 24, lines 30-35:
"A method according to claim 3 wherein a first transverse guide mark is near the proximal end of said spatula, a second transverse guide mark that is further from the proximal end of said spatula than said first transverse guide mark, and a third transverse guide mark that is further from the proximal end" should read -- A method according to claim 3 wherein said first transverse guide mark is near the proximal end of said spatula, a second transverse guide mark is further from the proximal end of said spatula than said first transverse guide mark, and a third transverse guide mark is further from the proximal end of --.

Claim 9, column 25, line 27:
"plane defined by said planar wedge, and;" should read -- plane defined by said planar wedge; --.

Claim 9, column 25, lines 29-30:
"inserting said drill guide into said incision until said proximal end of the drill guide aligns with said first transverse guide mark on said spatula" should read -- inserting said drill guide into said incision until said proximal end of the drill guide aligns with a first transverse guide mark of said one or more transverse guide markings on said spatula --.

Signed and Sealed this
Twenty-eighth Day of June, 2011

David J. Kappos
*Director of the United States Patent and Trademark Office*

Claim 9, column 25, lines 35-37:
"further inserting said drill guide into said incision until said proximal end of the drill guide aligns with said second transverse guide mark on said spatula," should read -- further inserting said drill guide into said incision until said proximal end of the drill guide aligns with a second transverse guide mark of said one or more transverse guide markings on said spatula, --.

Claim 15, column 26, lines 23-25:
"A method according to claim 13 wherein a first transverse guide mark is near the proximal end of said spatula, a second transverse guide mark that is further from the proximal end of said spatula than said first transverse guide mark, and a third transverse guide mark that is further from the proximal end" should read -- A method according to claim 13 wherein said first transverse guide mark is near the proximal end of said spatula, a second transverse guide mark is further from the proximal end of said spatula than said first transverse guide mark, and a third transverse guide mark is further from the proximal end of --.